US008676602B2

(12) United States Patent
Broselow

(10) Patent No.: US 8,676,602 B2
(45) Date of Patent: *Mar. 18, 2014

(54) COMPUTERIZED METHOD OF DETERMINING MEDICAL TREATMENT VALUES

(71) Applicant: EBroselow, LLC, Blacksburg, VA (US)

(72) Inventor: James Broselow, Hickory, NC (US)

(73) Assignee: eBroselow LLC, Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/904,725

(22) Filed: May 29, 2013

(65) Prior Publication Data

US 2013/0253946 A1    Sep. 26, 2013

Related U.S. Application Data

(63) Continuation-in-part of application No. 13/175,668, filed on Jul. 1, 2011, now Pat. No. 8,494,875, and a continuation-in-part of application No. 12/203,218, filed on Sep. 3, 2008, now abandoned.

(51) Int. Cl.
  *G06Q 50/00* (2012.01)
(52) U.S. Cl.
  USPC ...... 705/2; 705/3; 702/19; 604/416; 434/276; 128/898
(58) Field of Classification Search
  USPC ............. 705/3, 2; 702/19; 604/416; 434/276; 128/898
  See application file for complete search history.

(56) References Cited

U.S. PATENT DOCUMENTS

| 4,926,885 | A  | * | 5/1990  | Hinkle          | 128/898 |
| 5,915,971 | A  | * | 6/1999  | Ramsay et al.   | 434/276 |
| 6,508,801 | B1 | * | 1/2003  | Fineberg        | 604/416 |
| 6,804,656 | B1 | * | 10/2004 | Rosenfeld et al.| 705/3   |
| 7,555,435 | B2 | * | 6/2009  | Ball et al.     | 705/2   |
| 7,657,443 | B2 | * | 2/2010  | Crass et al.    | 705/2   |
| 7,747,454 | B2 | * | 6/2010  | Bartfeld et al. | 705/3   |
| 7,809,585 | B1 | * | 10/2010 | Ghouri          | 705/3   |

(Continued)

OTHER PUBLICATIONS

Google search, Dec. 3, 2013.*

(Continued)

*Primary Examiner* — Dilek B Cobanoglu
(74) *Attorney, Agent, or Firm* — Shumaker, Loop & Kendrick, LLP

(57) ABSTRACT

A computerized method of providing patient treatment values in real time, including the steps of providing a computer database having a plurality of predetermined patient selection criteria, patient condition categories, and drug selection, dosing values and related information, and providing an input device in communication with the computer database for inputting one or more of the patient selection criteria, patient condition categories and drug selection and dosing values and related information. A computer display in communication with the computer database and the input device is provided for displaying precalculated dosing values based on one or more inputted patient selection criteria, patient condition categories and dosing values and related information. One or more of the patient selection criteria, patient condition categories and treatment type is input by the input device into the computerized database provided in step (a) and associating a unique identifier with the inputted information. An appropriate drug dose is determined by the computer database, based on one or more of the patient selection criteria, patient condition categories and drug dosage values. The unique identifier is then used to communicate the appropriate drug dosage for administration to the patient.

19 Claims, 25 Drawing Sheets

(56) References Cited

U.S. PATENT DOCUMENTS

| | | | |
|---|---|---|---|
| 8,224,583 B2 | 7/2012 | Vaidya et al. | |
| 8,321,244 B2 | 11/2012 | Gaziano | |
| 2002/0169636 A1* | 11/2002 | Eggers et al. | 705/3 |
| 2005/0216203 A1* | 9/2005 | Vaidya et al. | 702/19 |

OTHER PUBLICATIONS

Google patents search, Mar. 22, 2013.
Google European patents search, Mar. 22, 2013.

* cited by examiner

| 3kg | 4kg | 5kg | 6-7kg | 8-9kg | 10-11kg | 12-14kg | 15-18kg | 19-23.3kg | 24-29kg | 30-36kg |

QuickDose
15-18 kg

- RESUSCITATION
INFUSIONS
ANAPHYLAXIS
RSI
SEIZURES
RESPIRATORY MEDS
FLUID & BLOOD THERAPY
REHYDRATION THERAPY
ELECTROLYTE ABNORMAL
DKA
BURNS
TOXICOLOGY
GASTROINTESTINAL AGENTS
STEROIDS
INTERCRANIAL PRESSURE
CHEMICAL WEAPONS
PRESCRIBING GUIDE
{QUICK REFERENCE} ▷
{ANTIBIOTICS} ▷
{PAIN & SEDATION} ▷
- NEWBORN RESUSCITATION
DOSING KEY
TRADE/GENERIC INDEX

| ADENOSINE 1st DOSE IV | 0.1 mg/kg DOSE | | | | | | | (ADENOCARD) |
|---|---|---|---|---|---|---|---|---|
| | | | | | | | 15-18kg | |
| | | | | | | | 1.7 mg | |
| 3 mg/mL. | | | | | | | 0.57 mL | |

PUSH DIRECTIONS
IVP RAPIDLY OVER 1-2 SECONDS, FOLLOW WITH A RAPID BOLUS 5-10 mL NORMAL SALINE (NS) IVP. FOLLOW WITH SECOND DOSE OF 0.2 mg/kg IF UNSUCCESSFUL.

REMARKS
NOTE: TRY TO PLACE PATIENT'S IV ACCESS CLOSE TO THE HEART (e.g. ANTECUBITAL) SINCE PLACEMENT IN OTHER VEINS MAY RESULT IN TREATMENT FAILURE.
BRONCHOSPASM AND RESPIRATORY FAILURE MAY OCCUR IN ASTHMATIC PATIENTS, WATCH FOR RESPIRATORY DISTRESS.

FIG. 6

| 3kg | 4kg | 5kg | 6-7kg | 8-9kg | 10-11kg | 12-14kg | 15-18kg | 19-23kg | 24-29kg | 30-36kg |

| RESUSCITATION | GUIDE FOR PEDIATRIC RESUSCITATION AND EMERGENCY INFUSIONS - (15-18 kg) |
|---|---|

- RESUSCITATION
- INFUSIONS
- ANAPHYLAXIS
- RSI
- SEIZURES
- RESPIRATORY MEDS
- FLUID & BLOOD THERAPY
- REHYDRATION THERAPY
- ELECTROLYTE ABNORMAL
- DKA
- BURNS
- TOXICOLOGY
- GASTROINTESTINAL AGENTS
- STEROIDS
- INTERCRANIAL PRESSURE
- CHEMICAL WEAPONS
- PRESCRIBING GUIDE
- (QUICK REFERENCE) ▷
- (ANTIBIOTICS) ▷
- (PAIN & SEDATION) ▷
- •NEWBORN RESUSCITATION
- DOSING KEY
- TRADE/GENERIC INDEX

| FIRST LINE DRUGS | (15-18 kg) - SELECTED | |
|---|---|---|
| MEDICATION | (mgs) | DOSE IN mLs |
| ADENOSINE | | |
| CONCENTRATION - 3mg/mL | | |
| FIRST DOSE | 1.7mg | 0.57 mL |
| SECOND DOSE | 3.4 mg | 1.1mL |
| AMIADATONE REFERENCE IV | | |
| CONCENTRATION - 50mg/mL | 400mg | 1.5 mL |
| (DILUTE DOSE WITH 32 mL 5% DEXTROSE IN WATER) | | |
| ATROPINE REFERENCE IV | | |
| CONCENTRATION - 0.1mg/mL | 0.33mg | (IV) 3.3 mL |
| ATROPINE ET | | |
| CONCENTRATION - 0.4mg/mL | 0.3mg | (ET) 1.2 mL |
| BICARBONATE REFERENCE IV | | |
| CONCENTRATION - 1mg/mL | 16.5mg | 16.5 mL |
| EPINEPHRINE REFERENCE IV | | |
| CONCENTRATION - 0.1mg/mL (1:10,000) | 0.17mg | (IV) 1.7 mL |
| EPINEPHRINE ET | | |
| CONCENTRATION - 0.1mg/mL (1:10,000) | 0.17mg | (ET) 1.7 mL |
| WEIGHT (15-18 KG) | | |

PAGE TOP ◁

| Alphabetical List | << Previous Page / | Amiodarone Infusion IV - 3 mg/mL | | | | | | |
|---|---|---|---|---|---|---|---|---|
| ▪ Resuscitation | >> Click here for Amiodarone Mixing Instructions: | | | | | | | |
| ▪ Newborn Resuscitation | Amiodarone *Infusion IV - 3 mg/mL* | | | | | | | (CORDARONE) |
| Antibiotics | | 5 kg | | | | | | |
| Infusions | 5 mcg/kg/min | 0.5 mL/hr | | | | | | |
| Anaphylaxis | 6 mcg/kg/min | 0.6 mL/hr | | | | | | |
| RSI | | | | | | | | |
| Seizures | 8 mcg/kg/min | 0.8 mL/hr | | | | | | |
| Fluid & Blood Therapy | 9 mcg/kg/min | 0.9 mL/hr | | | | | | |
| Rehydration Therapy | | | | | | | | |
| Electrolyte Abnormal | /min | 1 mL/hr | | | | | | |
| | /min | 1.1 mL/hr | | | | | | |
| | /min | 1.2 mL/hr | | | | | | |
| | /min | 1.3 mL/hr | | | | | | |
| | /min | 1.4 mL/hr | | | | | | |
| | /min | 1.5 mL/hr | | | | | | |
| | nance Rate | 21 mL/hr | | | | | | |

164

160

Artemis App camera captures Artemis Code

[BY WEIGHT] [BY TAPE COLOR]
- 5kg
- 6-7kg
- 8-9kg
- 10-11kg
- 12-14kg

○ Alphabetical List  >
○ Search  >
○ By Catagory  >
○ Recently Viewed  >

162 se Reactions
ecipitate or worsen arrhythmias (torsades, atropine resistant bradycardia, heart block, paroxysmal
ular tachycardia).
nsion with IV product (16% of patients) may be fatal.
ardia and AV block may occur - temporary pacemaker should be available.
europathy and/or optic neuritis may occur and may progress to blindness.
dial depression, CHF, hypothyroidism, severe hepatic toxicity, nausea, vomiting, interstitial pneumonitis
lebitis.

indications and Warnings
Warning: Reserve for use in life-threatening arrhythmias refractory to other therapies due to high
ce of toxicity (may be fatal).
Warning: Patients should be hospitalized for initiation of therapy and loading dose administration.
indicated in patients with severe sinus node dysfunction; marked sinus bradycardia, 2 or 3 AV bloc;
nic shock; bradycardia-induced sycope (except if pacemaker is placed).

| BY WEIGHT | | BY TAPE COLOR | | | | | | | |
|---|---|---|---|---|---|---|---|---|---|
| Amiodarone *Infusion IV - 3 mg/mL* | | | | | | | | (CORDARONE) | |
| | | 5kg | | | | | | | |
| 5 mcg/kg/min | | 0.5 mL/hr | | | | | | | |
| 6 mcg/kg/min | | 0.6 mL/hr | | | | | | | |
| 8 mcg/kg/min | | 0.8 mL/hr | | | | | | | |
| 9 mcg/kg/min | | 0.9 mL/hr | | | | | | | |
| 10 mcg/kg/min | | 1 mL/hr | | | | | | | |
| 11 mcg/kg/min | | 1.1 mL/hr | | | | | | | |
| 12 mcg/kg/min | | 1.2 mL/hr | | | | | | | |
| 13 mcg/kg/min | | 1.3 mL/hr | | | | | | | |
| 14 mcg/kg/min | | 1.4 mL/hr | | | | | | | |
| 15 mcg/kg/min | | 1.5 mL/hr | | | | | | | |
| Mainetnance Fluid Rate | | 21 mL/hr | | | | | | | |

| Adverse Reactions |
|---|
| ■ May precipitate or worsen arrhythmias (torsades, atropine resistant bradycardia, heart block, paroxsmal ventricular tachycardia). |
| ■ Hypotension with IV product (16% of patients) may be fatal. |
| ■ Bradycardia and AV block may occur - temporary pacemaker should be available. |
| ■ Optic neuropathy and/or optic neuritis may occur and may progress to blindness. |
| ■ Myocardial depression, CHF, hypothyroidism, severe hepatic toxicity, nausea, vomiting, interstitial pneumonitis and phlebitis. |

| Contraindications and Warnings |
|---|
| ■ Boxed Warning: Reserve for use in life-threatening arrhythmias refractory to other therapies due to high incidence of toxicity (may be fatal). |
| ■ Boxed Warning: Patients should be hospitalized for initiation of therapy and loding dose administration. |
| ■ Contraindicated in patients with severe sinus node dysfunction; marked sinus bradycardia, $2^o$ or $3^o$ AV block |

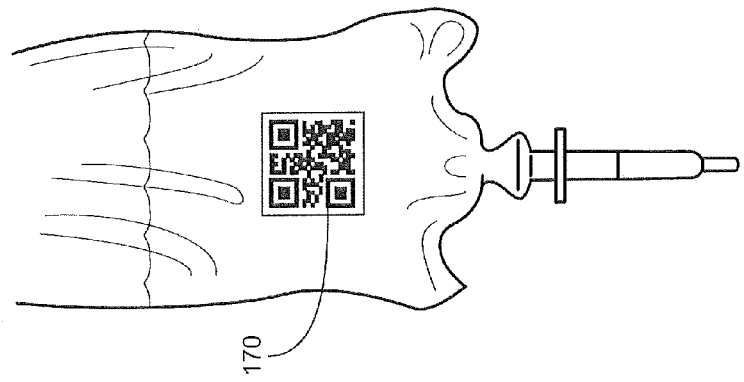
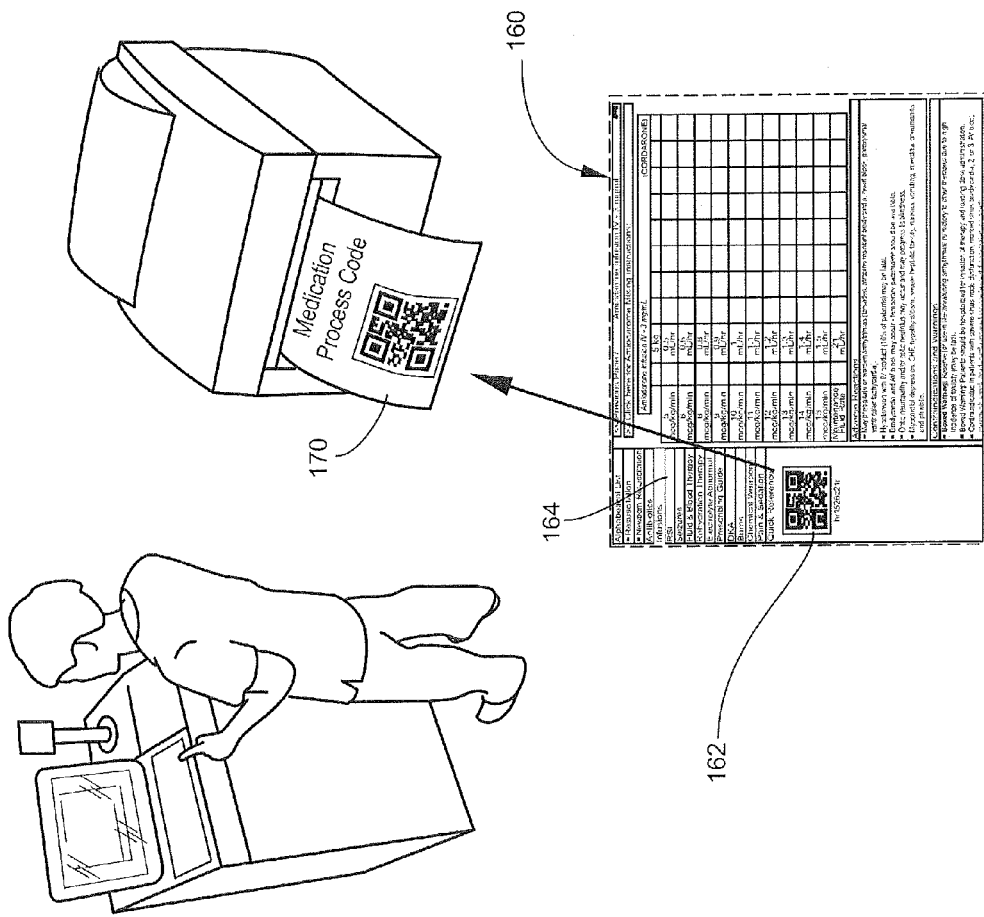
Fig. 21

COMPUTERIZED METHOD OF DETERMINING MEDICAL TREATMENT VALUES

TECHNICAL FIELD AND BACKGROUND OF THE INVENTION

This invention relates to a computer-based method of determining medical treatment values that takes into account present medical practices and anticipated changes in medical practices, particularly those intended to reduce drug dosing errors and the time required to accurately determine medical treatment values, such as drug dosages.

Ordering appropriate doses of medications for various indications is a complex, error prone process. Each drug has its own unique therapeutic profile which includes its various dosage forms, routes of administration, duration of action and potency. Certain drugs also have specific instructions related to exposure to light, safe handling, secure storage, and safe and secure disposal after use. Some of these guidelines are mandated by regulatory or accrediting agencies. Routes of administrations are varied, and including oral pills or liquids, parenteral IV or IM routes including infusions, aerosols, intra nasal, nasogastric tubes, and the like. Writing a prescription for an oral tablet, for example, might include determining the tablet strength most appropriate to the total amount to be administered, whether to take half a pill, whole pill or one and a half pills, the frequency of administration, expressed as 3 times per day or every 6 hours, etc. This information is conveyed as text on written or electronic prescriptions in a standard format such as: Hydralazine 50 mgs ½ tablet three times per day followed by the duration of therapy, if limited.

This system was well suited to past medical practice regimes, in which patients tended to see the same doctor for most conditions, and the doctor had a limited number of drugs that could be prescribed on a regular basis. When this patient entered a hospital for specialized care, that same doctor would frequently visit the patient along with the specialist involved and would help assure a smooth continuum of care. This situation has changed drastically as the number of medications and indications have grown exponentially. In addition, the introduction of emergency departments and hospitalists along with hospital-based nurses has significantly changed the nature of medical practice, so that no one person can possibly know all of the potential medications that could be ordered and prescribed for any given patient. The bedside nurse is especially impacted because of the requirements to administer drugs correctly, explain potential side effects to the patient or families, and document knowledge of each drug administered as part of the hospital Joint Commission and other regulatory and compliance mandates.

The substantial scope and breadth of the potential information involved is overwhelming, especially when one considers that there is almost no time for a busy nurse to research the totality of the relevant information in real time at the bedside. Part of the solution is to develop a coding system that facilitates immediate, real time access to a drug database that encompasses the totality of relevant information presented in a concise and clinically relevant way. In addition to these general changes, the hospital environment is rapidly evolving from a documents-based information to digital systems. This means that information presented in text formats would need to be read and then entered as digital data so that it can be accessed appropriately anywhere in the electronic record. The problems caused by this disconnect between text-based systems and digital ones is best demonstrated when a patient goes from their home or nursing facility to a hospital. There, the receiving institution tries to "reconcile" the medications to decide which should be continued or modified during the period of treatment by the receiving institution. For example, a nurse may be required to read, understand and implement a treatment regimen based on a list of medications and doses written on scraps of paper brought in by a patient, or a lengthy list of medications from a nursing home. Scanning a written list does enter the information into the medical record, but not in an electronically usable format since it is not granular, digital information. Even if legibility is not an issue, the physician who must make the final prescribing decisions needs to know that each medication to be continued is in the appropriate dose for the particular circumstances of the hospital stay.

Since a hospitalist will be seeing patients usually treated by many different physicians it is not possible to know the nuances of dosing represented by the drug list being presented. Similarly, the physician may delegate the responsibility of dose checking to a nurse or pharmacist involved with that patient's care. There is clearly a need to simplify and automate this entire process both to decrease errors and to reduce the amount of time and professional assets that are involved.

The solution is to develop a coding system that recognizes a drug name, dose and frequency of administration so that an entire prescription can be conveyed by a single code, thus allowing the information to be entered by a barcode reader into an electronic medication administration record ("eMar"). The eMar then translates the code back into the original text, allowing rapid evaluation of the need to continue the medication or to modify the dosages. Also, prescriptions with such a code displayed could digitally convey the key information to a pharmacy computer, again helping automate the process and reduce the need to read the writing on the prescription itself. Using this system, prescriptions can be written by a single code number or modified by changing a single digit of the code without requiring the entire information to be rewritten. Each change in code entered thus results in a new barcode. The code also facilitates direct communication of, for example, side effects, indications and the like directly from the medication to the patient. When required, the information can be translated into a specific language for each patient. At the hospital level this capability would help with meeting meaningful use requirements for optimum reimbursement without requiring significant time to be incurred by nurses looking up information in standard references for medications that they may not be familiar with. One aspect of the solution is to develop a medication potency scale such as "level 1-10" that delineates where a prescription or drug order resides within the entire range of appropriate dosage for a particular medication and indication. A typical prescription would be for the middle of the range. As an example, Hydralazine Level 5 prescription would then connote all of the information illustrated above. Since the drug itself has an NDC Code as well, all of the information can then be condensed into a single barcode that can immediately enter the entire drug profile into the eMar. Conversely, any prescription with the NDC Code or other unique identification associated with it can be scanned and expressed as text for communication to a patient or pharmacist. Writing prescriptions for oral medications is straightforward, since many times the order is for products that have already been produced, or can be reconstituted in a straightforward manner.

However, frequently in hospital settings more complex issues surface when ordering, preparing and administrating medications in real time acute clinical settings. An example is ordering, preparing and administering medications for delivery as infusions. Many critical medications are best delivered by large and small pump infusion devices. There are various reasons why this is true, but one of the principal functions of a pump infusion device is to control the rate of delivery of potent medications in infants, pediatric patients and adults. The typical infusion pump is "programmable" at the bedside, allowing data input including the name of the medication, concentration, volume, etc. Infusion pumps have both manual settings for simple parameters such as mLs per minute or per hour and volume.

Because of errors that have occurred with setting these pumps in actual clinical situations, software has been developed that includes "drug libraries" which have standardized medications, concentrations, delivery settings and alerts that indicate if a drug is being delivered outside of accepted ranges based on patient's weight and clinical setting. These libraries tend to be specific for various aspects of clinical care and settings such as the NICU, ICU, Surgery, etc. Typically there may be up to 9-10 libraries representing the full spectrum of care in a large medical center. Each pump has to be individually programmed with the initial library information and updated as needed. They can also be programmed by WiFi as part of an enterprise electronic medication delivery system. Considerable time, resources and expenses are associated with this process. In addition, when infusions are mixed at the pharmacy level and arrive at the bedside, the library must be accessed and the particular drug, concentration, and volume entered into to the appropriate library in the pump. This process is subject to errors, to the extent that some hospitals actually have special teams that go to the point of care to "set the pumps" in attempt to minimize potential errors from a bedside nurse setting the pump incorrectly.

Also, in research situations with new drugs or new doses for existing drugs, the programmed library rarely includes these drugs. There is also clearly a need to simplify and streamline this process as well. Ordering or double-checking infusions is particularly problematic since orders are typically given in micrograms/kg/minute, and the pumps are set for mLs per hour. There is no simple way of conveying the potency of drug delivery at any particular time due to the fact that the doses as ordered might be a small dose (2 mics/kg/minute) for one drug and indication, and a large dose for another. A 1-10 scale as described above would greatly facilitate ordering and communication in this error prone area.

Recently a system has been developed that standardizes the indication, dose, dilution, and rate of administration, as exemplified in Patent Application Publication US 2011/0264462, to James B. Broselow. Because the Broselow system represents all of the parameters needed to do an initial infusion pump setting, there is now the possibility to automate the entire process. A database can be developed that contains a specific identifier (number and/or letter) for every combination of drug, starting dose and dose range for each indication, dilutions and final volume.

This "identifier" can thus represent all of the information needed to automatically set the pump to an initial setting appropriate for that patient's specific clinical need. Included in this identifier is the potency represented by the "scale" described above. Software in the pump converts that number into a specific initial output and, with pumps containing drug libraries, it can also display drug name, output, etc. as if the library had been the source of the information. The potency at any point in time can be displayed on the pump itself by showing the scale either visually or as a number or percent. The identifier can be entered manually by a keyboard, wireless from a mobile device or an inline system or, preferentially, by barcode scanning or QR code capture directly into the device.

A digital system that includes an identifier number that encompasses all of the medical information needed to prescribe or deliver a dose of a particular drug is therefore needed. Such a system provides exact preparation and administration information when needed, presented as a barcode to communicate both to electronic medical systems as well as to specific delivery devices thus will allow automation of the entire process of medication delivery, reducing both errors and healthcare costs.

SUMMARY OF THE INVENTION

Therefore, it is an object of the invention to provide a system that permits the determination of medical treatment values without data entry.

It is another object of the invention to provide a computerized system that permits the identification of all of the independent variables that are needed to prescribe order, prepare and administer a medication for each drug, clinical variable, indication, route of administration, and potency while addressing therapeutic and/or regulatory and compliance requirements.

It is another object of the invention to provide a computerized system that permits input variables that are needed to prescribe order, prepare and administer a medication for each drug, clinical variable, indication, route of administration, and potency and to permit use of this information manually or by barcode scanning to identify the appropriate clinical activity.

It is another object of the invention to provide a computerized system that permits data input and output by means of a smart phone, such as the Apple iPhone, iPad, Blackberry or the many Android-equipped handheld devices.

It is another object of the invention to provide a computerized system that associates the output for each appropriate clinical activity with a unique identifier represented as a barcode.

It is another object of the invention to provide a computerized system that uses a unique barcode to communicate the entire process to a digital system to translate back into a clinically relevant readable format and/or to automatically set a medication delivery device such as an infusion pump.

It is another object of the invention to provide a computerized system that uses a relative potency scale to prescribe, order, or modify, or communicate medications orders or delivery irrespective of the relative strengths of each individual medication unit.

These and other objects and advantages of the invention are achieved by providing a computerized method of providing patient treatment values in real time, including the steps of providing a computer database having a plurality of predetermined patient selection criteria, patient condition categories, and drug selection, dosing values and related information, and providing an input device in communication with the computer database for inputting one or more of the patient selection criteria, patient condition categories and drug selection and dosing values and related information. A computer display in communication with the computer database and the input device is provided for displaying precalculated dosing values based on one or more inputted patient selection criteria, patient condition categories and dosing values and related information. One or more of the patient selection criteria, patient condition categories and treatment type is input by the input device into the computerized database provided in step (a) and associating a unique identifier with the inputted information. An appropriate drug dose is determined by the computer database, based on one or more of the patient selection criteria, patient condition categories and drug dosage values. The unique identifier is then used to communicate the appropriate drug dosage for administration to the patient.

According to another embodiment of the invention, the unique identifier comprises a barcode.

According to another embodiment of the invention, the plurality of predetermined patient selection criteria comprises body weight and a color indicative of a predetermined body weight range.

According to another embodiment of the invention, the unique identifier includes a barcode and the method includes the step of scanning the barcode with a barcode reader that outputs a signal to an input device indicative of the predetermined patient selection criteria, patient condition categories, and drug selection, dosing values and related information in the database.

According to another embodiment of the invention, the computer display comprises the display screen of an electronic handheld device.

According to another embodiment of the invention, the method including the step of utilizing the unique identifier to communicate the appropriate drug dosage for administration to the patient via an infusion pump.

According to another embodiment of the invention, the method includes the steps of utilizing the unique identifier to calculate and convert drug dosage information into an administration value, and communicating the appropriate drug dosage for administration to the patient to an electronically programmable infusion pump.

According to another embodiment of the invention, a computerized method of providing patient infusion treatment values for an infusion pump in real time is provided, and includes the steps of providing a computer database having a plurality of predetermined patient selection criteria, patient condition categories, and infusion selection, dosing, values and information, and providing an input device in communication with the computer database for inputting one or more of the patient selection criteria, patient condition categories and infusion selection and dosing values. A computer display in communication with the computer database and the input device is provided for displaying precalculated infusion dosing values based on one or more inputted patient selection criteria, patient condition categories and infusion pump dosing values, and one or more of the patient selection criteria, patient condition categories and treatment type is input into the computerized database and a unique identifier is associated with the inputted information. An appropriate infusion dose is calculated by the computer database based on one or more of the patient selection criteria, patient condition categories and infusion dosage. The unique identifier is then used to communicate the appropriate infusion dose for entry into the infusion pump.

According to another embodiment of the invention, the method includes the step of providing an electronic slider scale visible on the computer display and having a predetermined range indicating that the dosage is in the correct range of dosages for the particular patient based on that patient's individual characteristics as input in to the computer.

According to another embodiment of the invention, the unique identifier comprises a barcode.

According to another embodiment of the invention, the plurality of predetermined patient selection criteria comprises body weight and a color indicative of a predetermined body weight range.

According to another embodiment of the invention, the unique identifier is a barcode and the method includes the step of scanning the barcode with a barcode reader that outputs a signal to an input device indicative of the predetermined patient selection criteria, patient condition categories, and drug selection, dosing values and related information in the database.

According to another embodiment of the invention, the computer display is the display screen of an electronic handheld device.

According to another embodiment of the invention, the step of utilizing the unique identifier to communicate the appropriate infusion dose for entry into the infusion pump comprises the step of manually entering the appropriate infusion dose.

According to another embodiment of the invention, the step of utilizing the unique identifier to communicate the appropriate infusion dose for entry into the infusion pump includes the steps of scanning the barcode, electronically delivering the appropriate infusion dose to the infusion pump and electronically entering the appropriate infusion dose into the infusion pump.

According to another embodiment of the invention, the method includes the steps of printing a label having an image of the barcode thereon, and applying the label to an infusion bag associated with the patient.

BRIEF DESCRIPTION OF THE DRAWINGS

Some of the objects of the invention have been set forth above. Other objects and advantages of the invention will appear as the description of the invention proceeds when taken in conjunction with the following drawings, in which:

FIG. 6 is a representation of a chart showing the selected treatment doses for a selected medication and weight range according to an embodiment of the invention;

FIG. 9 is a representation of a listing of dosages for common medications for a given weight range according to an embodiment of the invention;

FIG. 10 is a representation of a prescribing guide according to an embodiment of the invention;

FIG. 11 is a representation of an antibiotics guide according to an embodiment of the invention;

FIG. 13 is representation of a listing of dosages for common antibiotics for a given weight range according to an embodiment of the invention;

FIG. 17 is a representation of the entry screen of FIG. 16, showing camera capture of the matrix, or two-dimensional barcode, often referred to by the trademark "QR" code;

FIG. 18 is a representation of the entry screen of FIG. 16, showing a 1-10 medication potency slider scale;

FIG. 19 is a representation of an application screen displaying infusion rates returned when the matrix barcode for Amiodarone is scanned;

FIG. 20 is a representation of an application screen displaying an infusion drug dosage obtained by scanning an NDC barcode;

FIG. 21 illustrates a step of the method that prints a matrix barcode label for placement on an infusion bag specific to the patient, drug and drug dosage;

DETAILED DESCRIPTION OF EMBODIMENTS OF THE INVENTION AND BEST MODE

Embodiments described herein set out a process for solving the problems of the prior art. First, the pharmacology of each acute drug is reviewed in advance as it relates to acute administration in children. Next, an interface is developed that allows all relevant information to be conveyed on a single screen. Third, a "dosing grid," is accessed with an exact grid for a particular child size by determining a code, for example, scanning an NDC barcode, from the drug. Scanning the drug helps to prevent transcription, reading and other human errors that can contribute to administering a dangerous or even fatal dose. A child's weight may also be entered, for example, scanned from a barcode on the armband or patient chart. If no weight barcode is present, putting the weights in zones would allow a single click or touched access that corrects grid. The zones may be represented by colors, for example. For all drugs with a single indication, these two scans would access the exact dose, conversion in milliliters, preparation and administration information, and other information. For a drug with multiple indications or treatments, scanning would then access as a screen that asks first to identify the correct indication or treatment. For example, dexamethasone is a steroid that is used in different doses for cerebral edema, airway edema croup, anti-inflammatory, anaphylaxis, etc. The screen would list these indications or treatments and could be selected by a mouse or touch screen to access all of the relevant information. In general, a single entry at most would be all that is required to determine the or verify a correct dose. A dosing grid would include that same indication so that anyone looking at the grid could see the drug name, patient weight, conversion in milliliters, dilution and administration time for that particular drug for that exact indication. With minimal searching, complex infusion mixing instructions could be simplified by simply stating how much to draw out of the vial and put into a bag of fluid. These instructions would be direct and simple without needing additional data entry and/or reference to a standard infusion calculation program.

A major advantage of scanning the NDC code is to ensure that all conversions and dilutions are based on the actual concentration and the amp. A recent well publicized error occurred in newborn twins, for example, when a huge dose of heparin was administered by mistake because a nurse thought the concentration of the vial was the concentration that she usually used, but in fact she put the wrong vial in the drawer. Scanning the vial as above would have prevented this error. Also recently, a child died in a children's hospital due to a ten-fold error in calcium being given. Again, a system such as the embodiments described above would have avoided this error. Indeed, the term "death by decimal point" has described this particular hazard that children face when being given medications.

Figure 1:
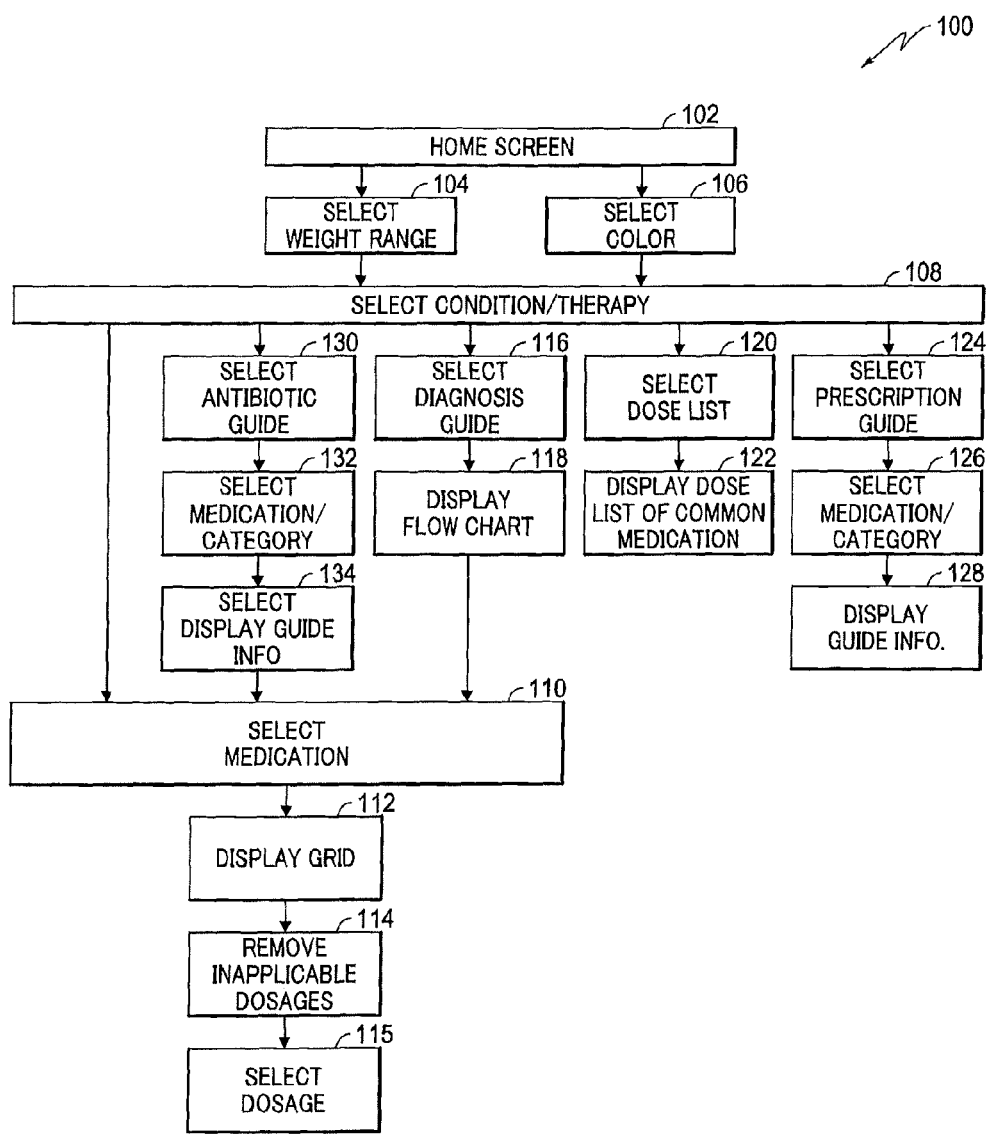
FIG. 1 is an illustration of a workflow method according to an embodiment of the invention.

Referring now specifically to the drawings, an entry screen is shown in FIG. 1 that permits the user to quickly determine a selected one of many values. The values are entered into the system as text during system development and maintenance. The system contains no values that are calculated by the system or that must be entered by the user during patient treatment. This prevents miscalculated values resulting from hasty, careless or mistaken data entry. The text values are entered, double-checked and verified in a controlled, non-patient, stress-free environment. The user is thus freed from the task of remembering and correctly entering values in an emergency situation.

The system is thus passive and user-friendly, highly graphical and operates in real time. Standardized formatting means that the user can quickly become familiar with the layout, thus further increasing speed and accuracy.

The application shown is a system and method particularly adapted for use in pediatric emergency situations commonly found in hospital emergency rooms and in EMS facilities or vehicles. Other applications of the system and method include general medical practice, geriatric care and veterinary care. A color-coding regime based on variables such as weight ranges may be used. Example embodiments are weight-based, but can be based on length correlated to lean body mass. In the application illustrated in FIG. 1, the user may start on the entry screen by picking a category, such as "resuscitation" based on the immediate observation by the user of the patient's condition and the needed intervention and "clicking" on the "Resuscitation" Category. The system may be further entered by knowing that the patient is a coded "purple", or may weigh or estimate the weight of the patient without regard to color coding. Clicking on the "Purple" box at the top of the chart immediately opens a table. Knowing the "color" of the patient, i.e., purple, yellow, etc., permits a wide range of treatment selections to be made without calculations, weight or age estimates.

Turning now to the drawings, FIG. 1 is an illustration of a workflow method according to an embodiment of the invention. Beginning with entry screen 102 either a weight range 104 or a color corresponding to that weight range 106 is selected. A condition or therapy is then selected at which point a number of options are available.

The most common option would be to simply select the medication 110, at which point a grid is displayed for that particular weight range 112 and inapplicable doses 114 are whited out or otherwise hidden. It is then a simple matter of selecting the dosage 115 at which point an administration flowchart 118 or prescription guide 128 for example can be displayed. Another option is to select a diagnosis or treatment guide 116 based on known symptoms, a flowchart showing next steps 118 can be displayed. If a medication is required, a link to the medication selection screen may be provided 110. Another option is to select a dose list for common medications 120 once the weight range is determined, a dose list of common medications for that weight range 122 may be displayed. That screen may link to a medication selection screen as well 110. Another option is to select a prescription guide 124 for a specific range of medications or categories. Once the medication or category is selected 126, guide information for that particular medication or category is displayed 128. Another option is to select an anthriotic guide 130 similar to selecting medication or dose list, a medication or category can be selected 132 and guide information for that particular antibiotic or family of antibiotics can be displayed 134. At this point, a specific antibiotic may be selected in the medication selection screen 110.

Figure 2:
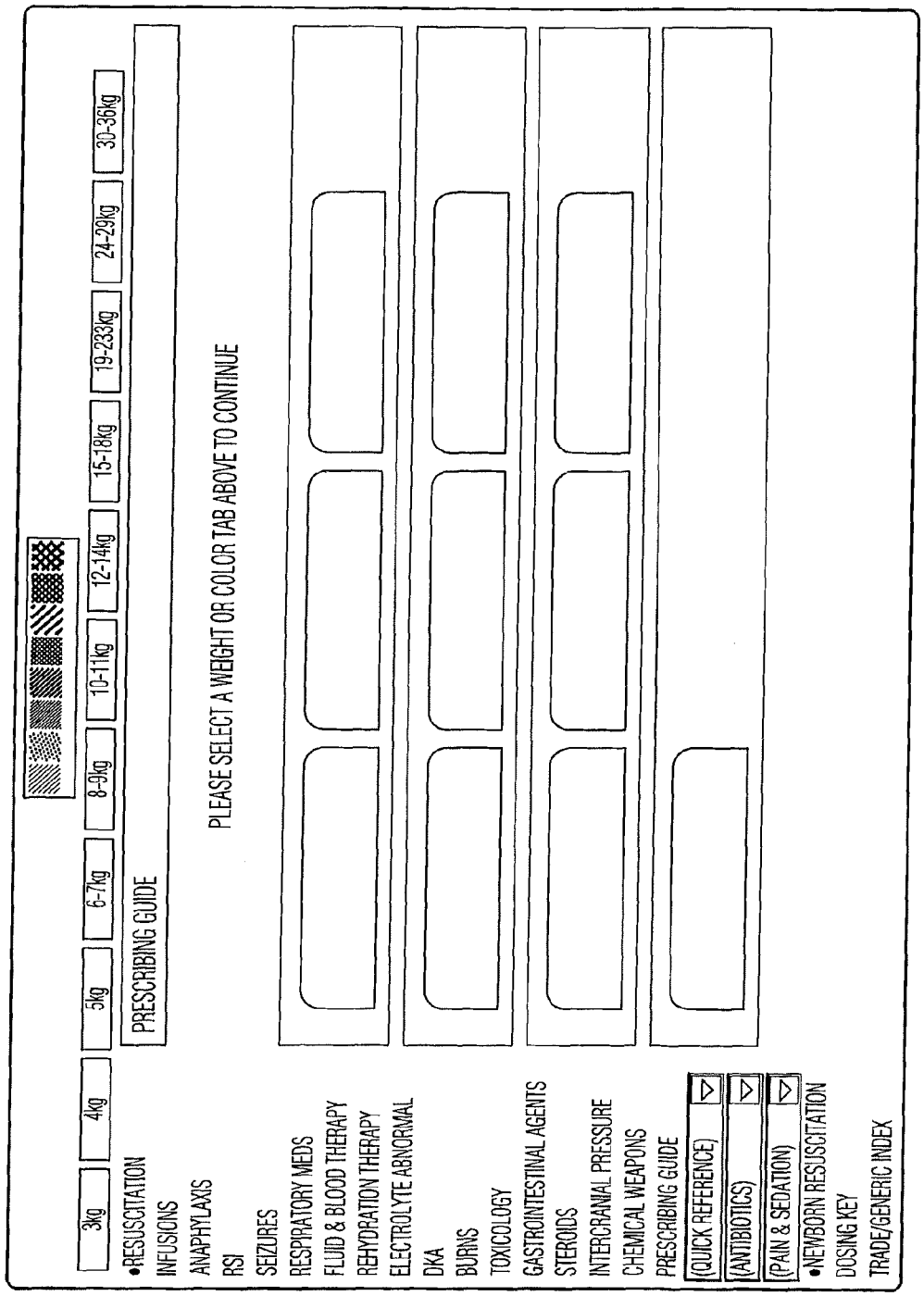
FIG. 2 is a representation of an entry screen according to an embodiment of the invention.

FIG. 2 is a representation of an entry screen 102 according to the above embodiment. In a single interface, weight ranges, color codes, common conditions and treatments and other options are available in a single screen.

Figure 3A:
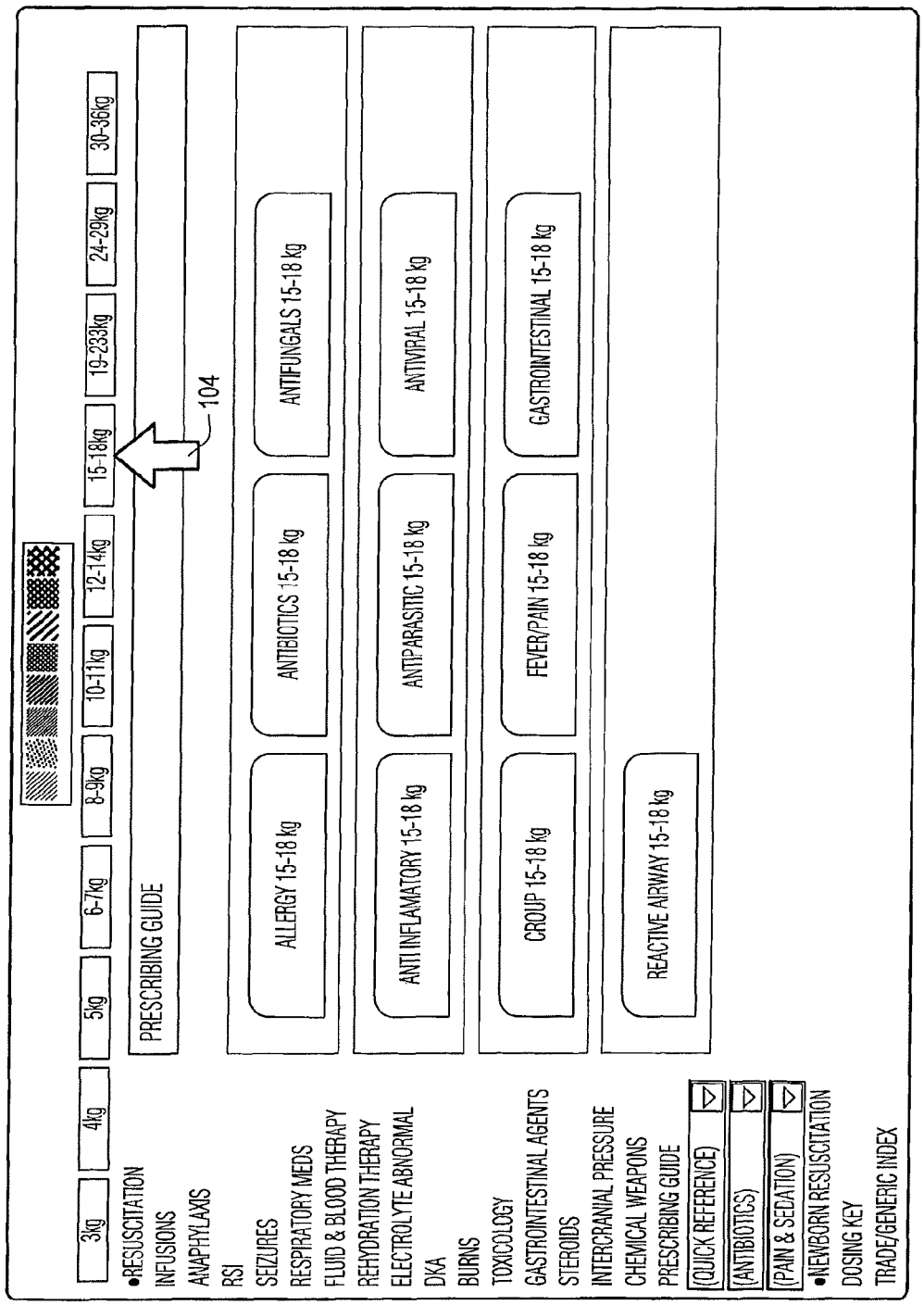
FIG. 3a is a representation of a weight selection step according to an embodiment of the invention.
Figure 3B:
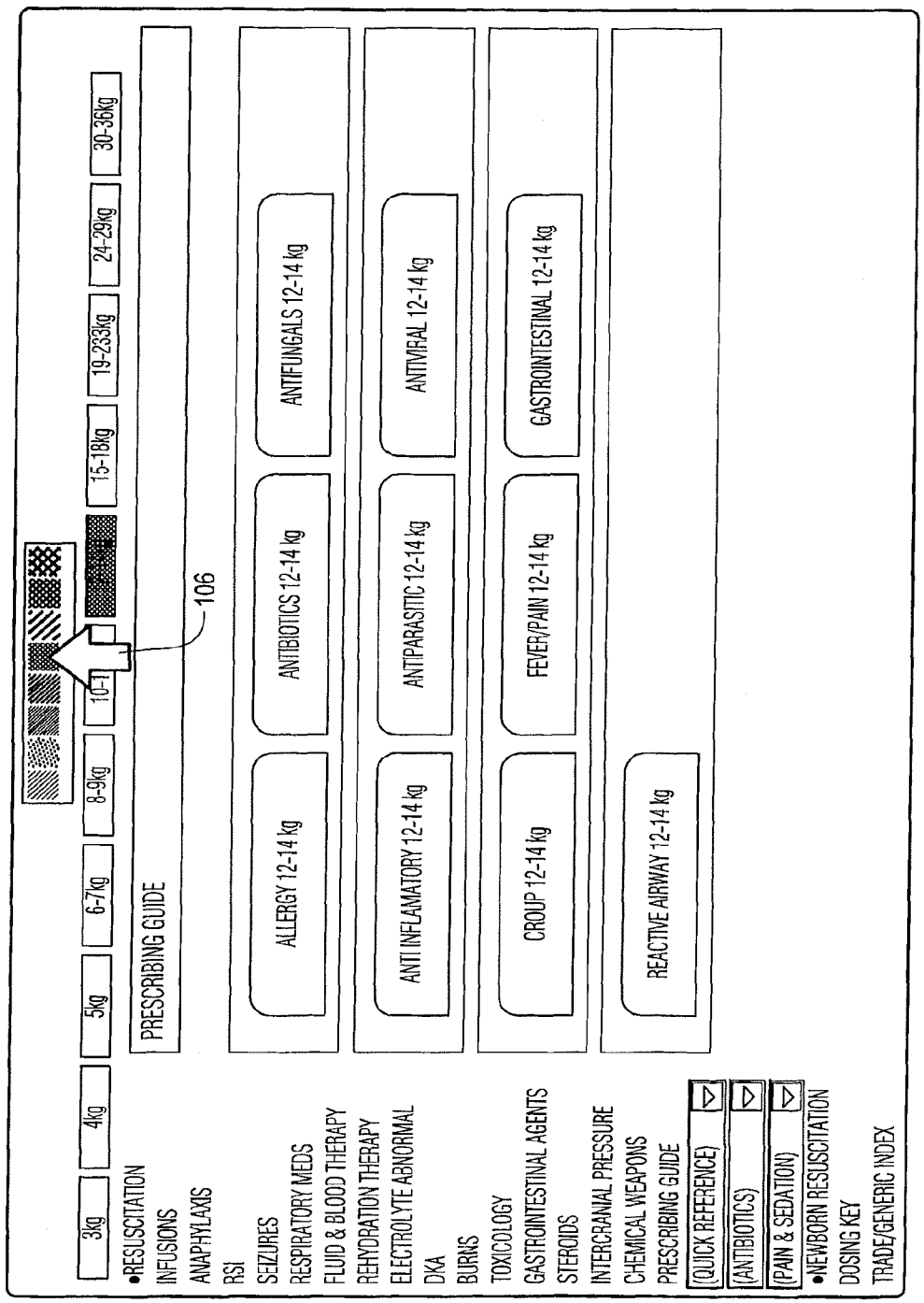
FIG. 3b is a representation of a color selection step according to an embodiment of the invention.

FIGS. 3a and 3b illustrate the selection process for weight ranges 104 and color codes 106, respectively. Once the weight range is selected, additional options such as prescribing guides for children of that particular weight range of color code are provided.

Figure 4:
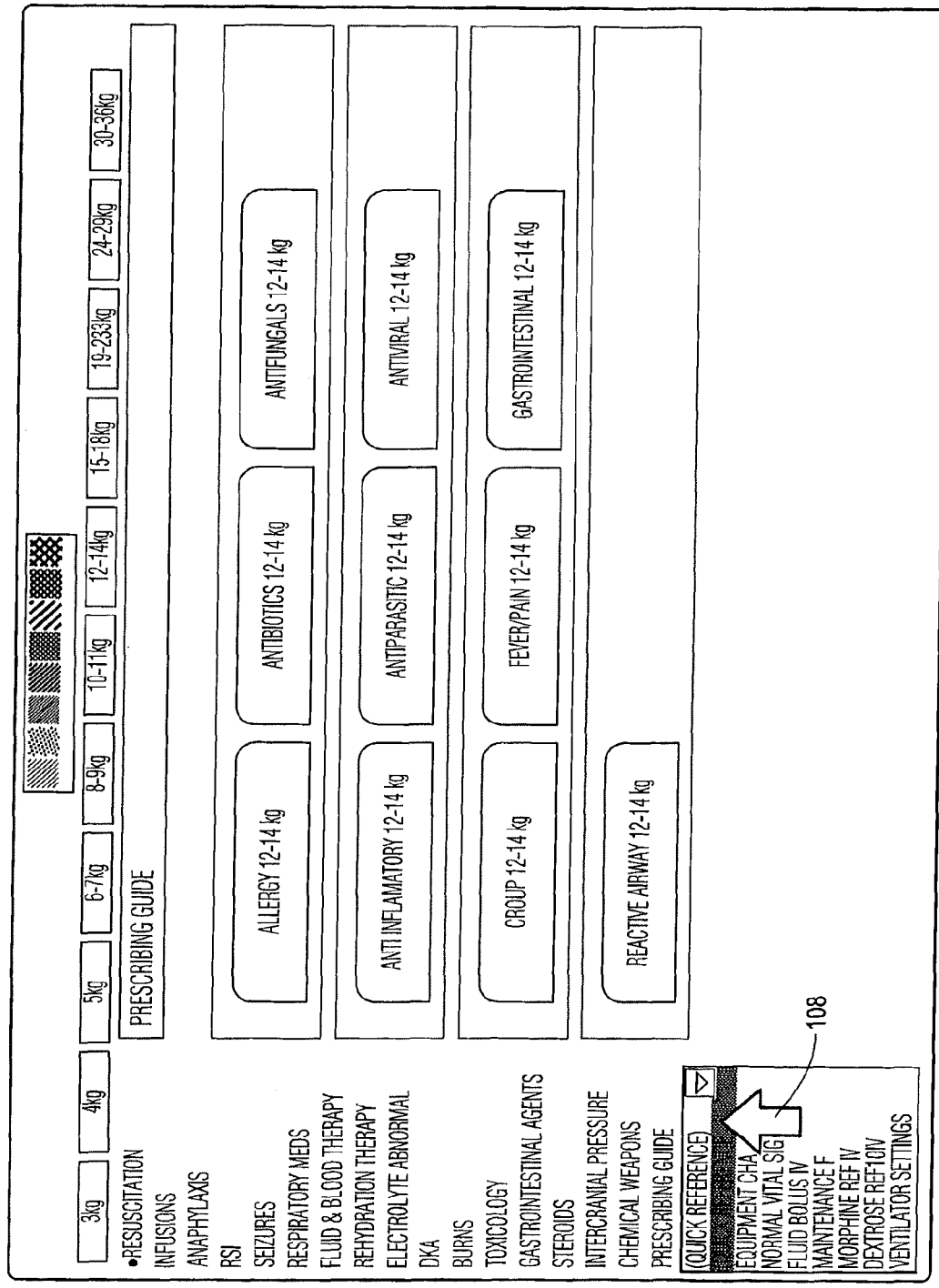
FIG. 4 is a representation of a treatment selection step according to an embodiment of the invention.

FIG. 4 shows additional options, for example, through a drop-down menu.

Figure 5:
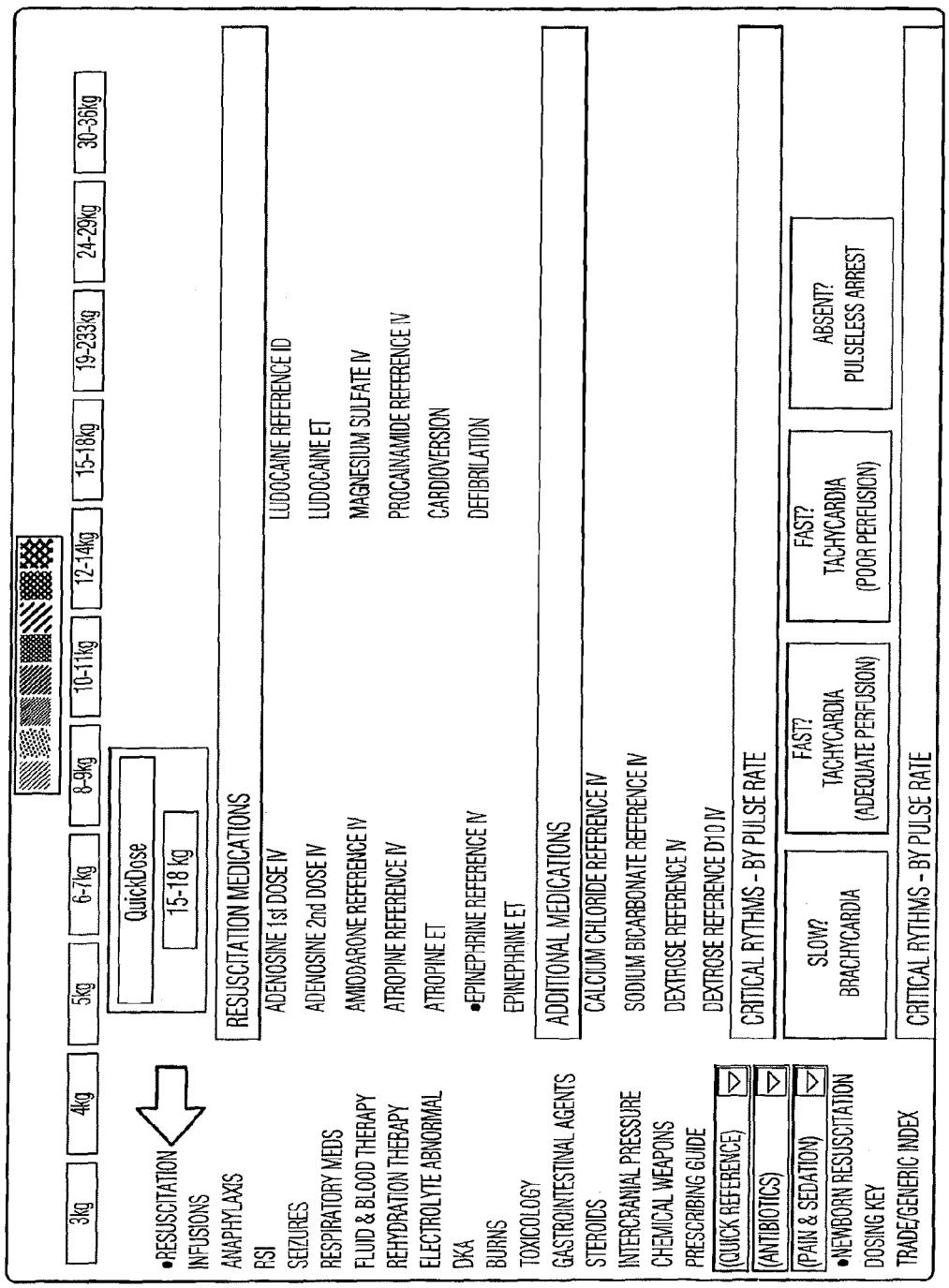
FIG. 5 is a representation of a medication selection step according to an embodiment of the invention.

FIG. 5 discloses a selection of condition or therapy 108. In this figure, a list of common medications for each selection condition or therapy is presented.

FIG. 6 shows a medication selection grid that includes the display of the correct dosage for a given drug and weight range 112 and also hides, whites out, or otherwise de-emphasizes other inapplicable ranges 114 to prevent errors.

Figure 7:
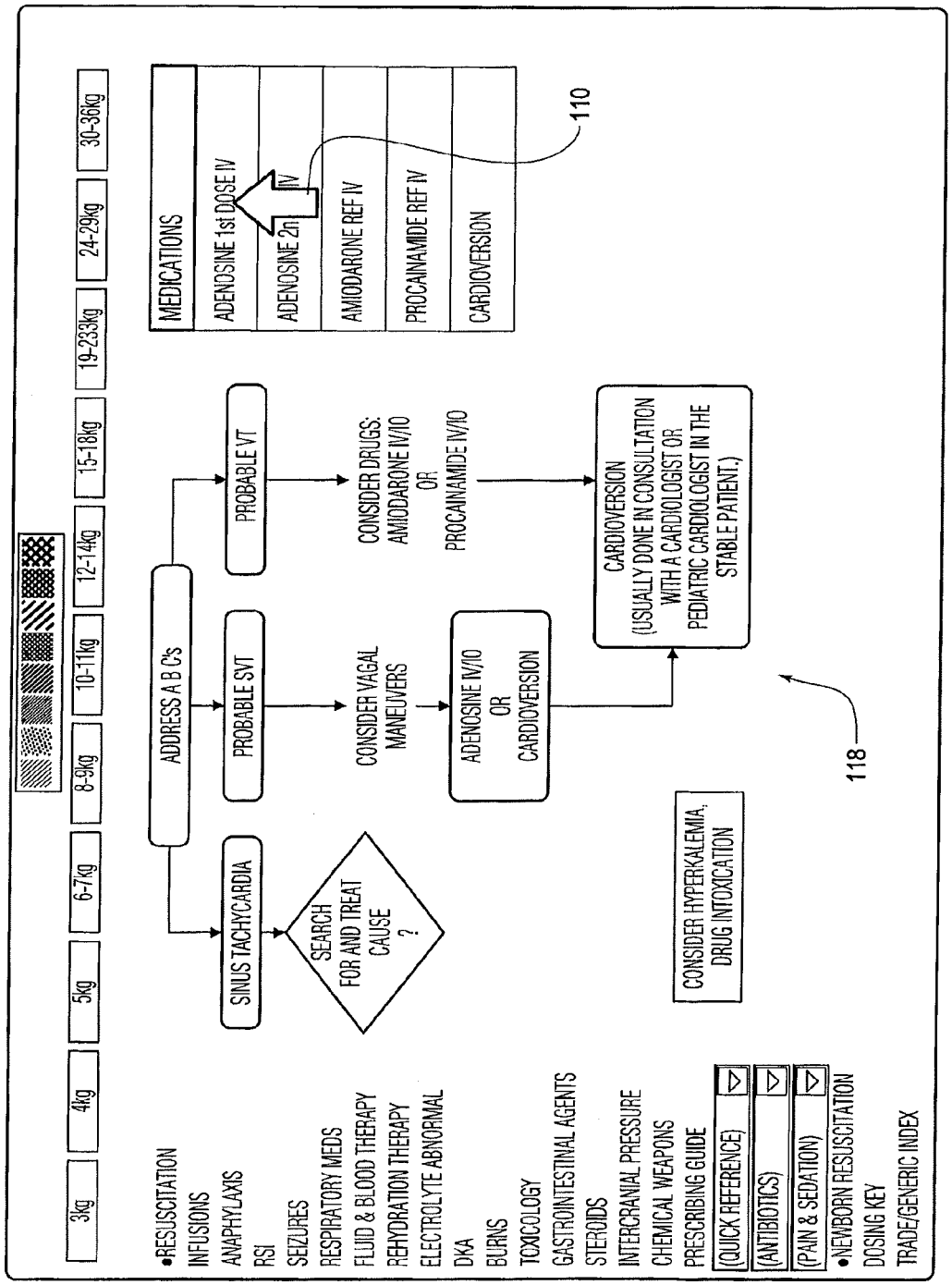
FIG. 7 is a representation of a diagnosis and treatment guide displaying a treatment flowchart according to an embodiment of the invention.

FIG. 7 shows a flowchart for diagnosis and treatments of specific symptoms 118, as well as referenced medications which link to the medication selection 110.

Figure 8:
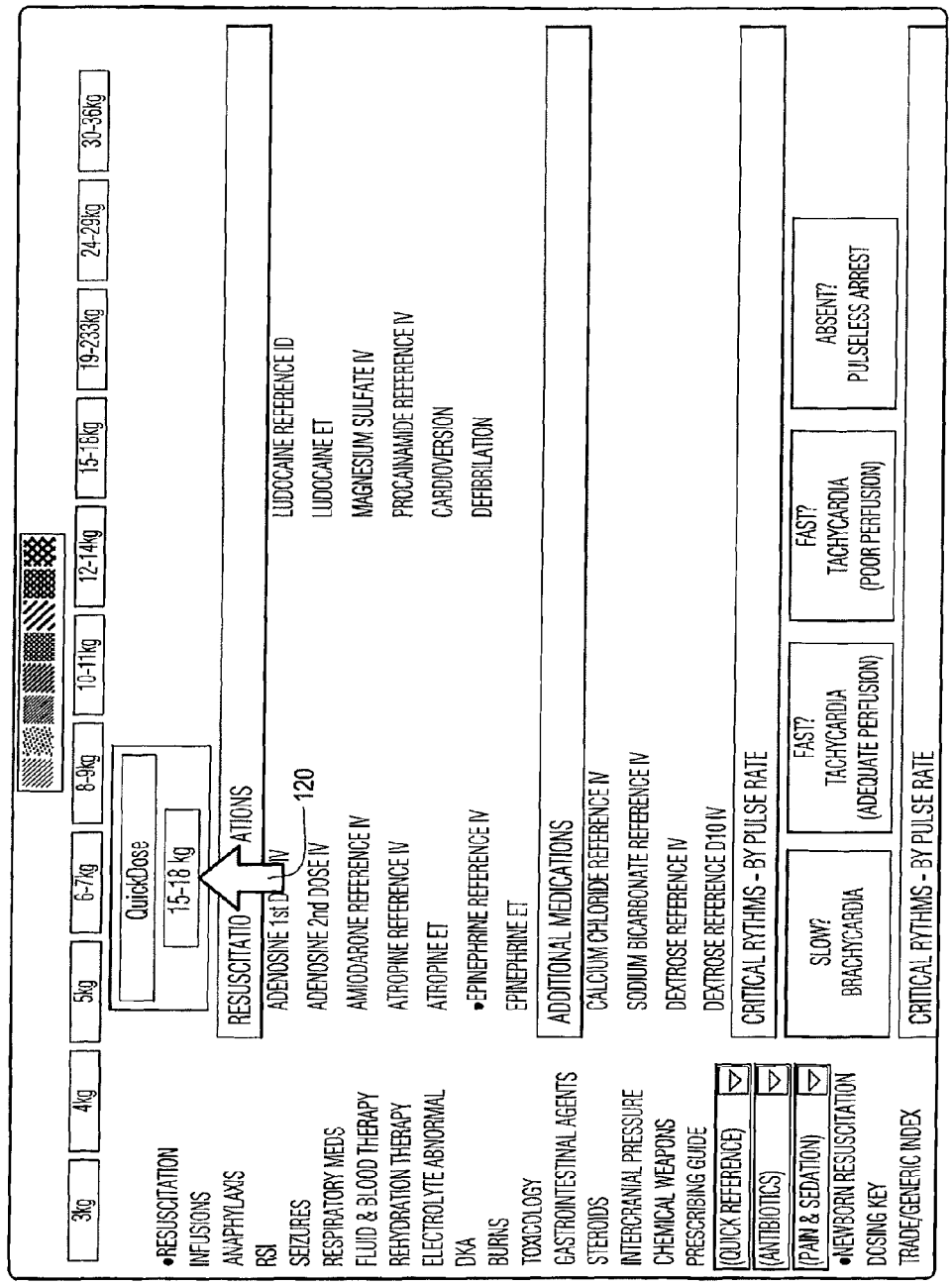
FIG. 8 is a representation of a listing of common medications for a given weight range according to an embodiment of the invention.

FIG. 8 shows a selection of the dose list for a 15-18 kg child 120.

As shown in FIG. 9, selecting this option will list common medications for the child's weight range and symptoms or treatment 122.

Figure 10:
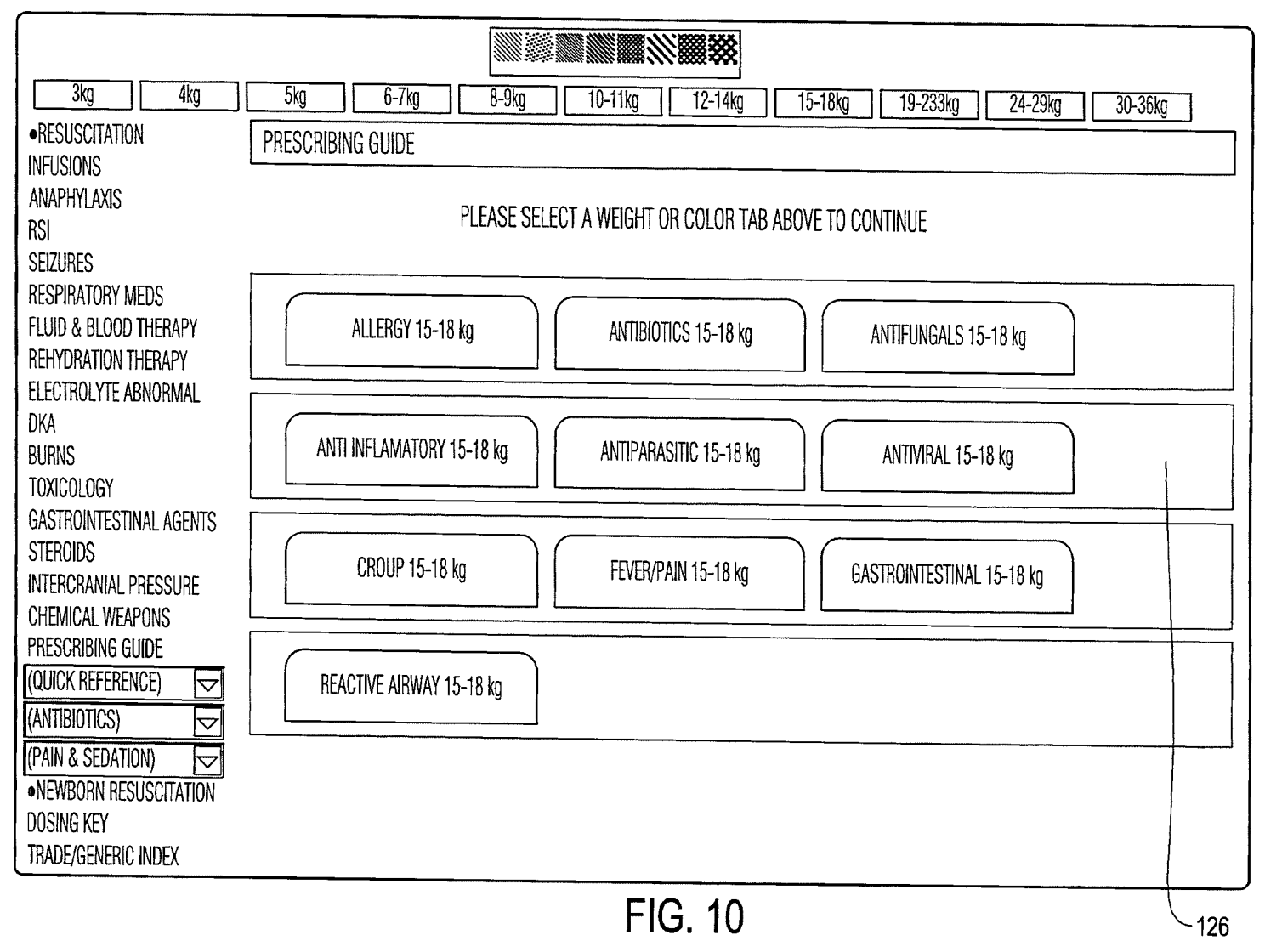

FIG. 10 shows a prescribing guide for common medications for a given weight range 126.

Figure 11:
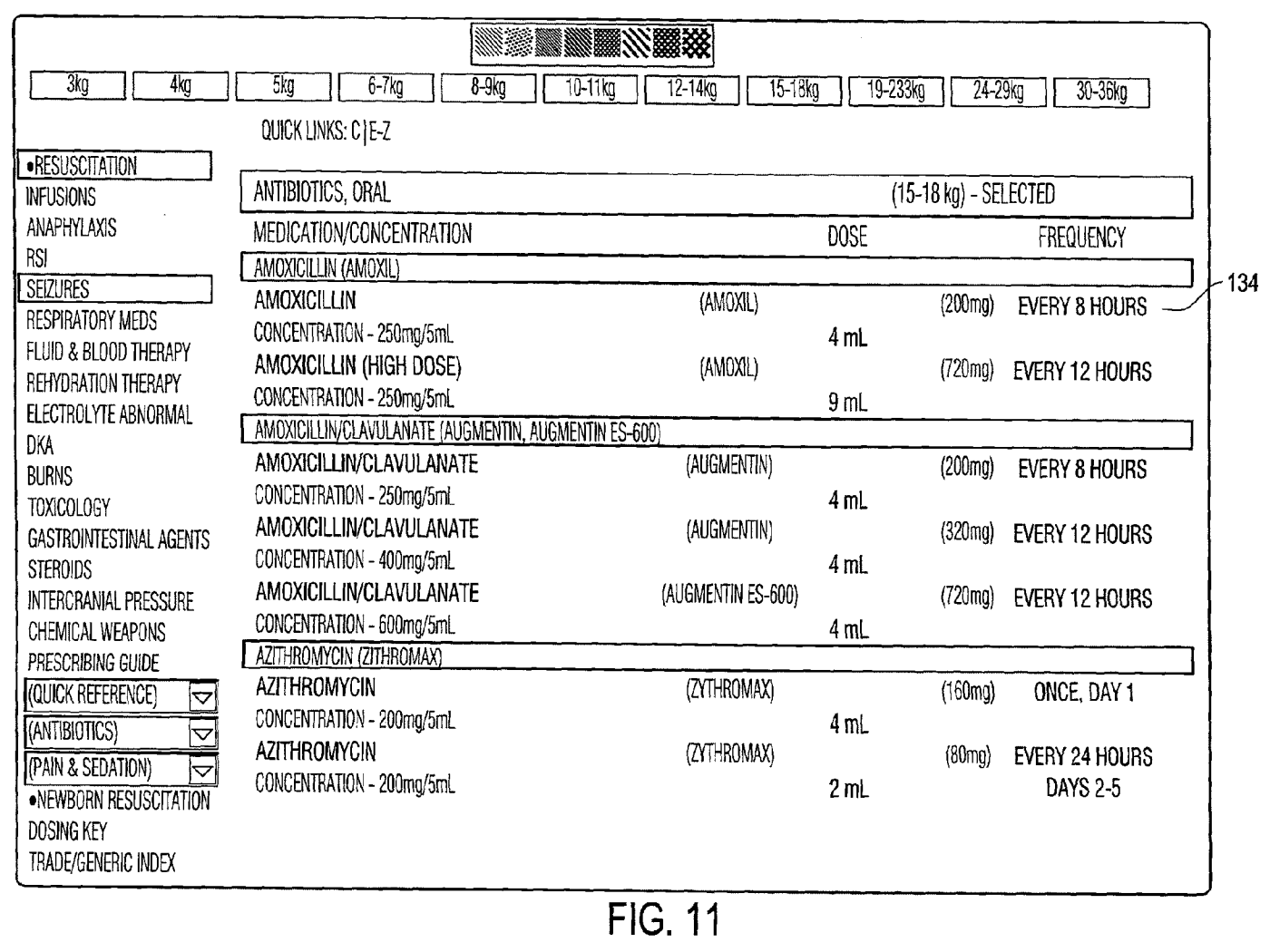

FIG. 11 discloses an antibiotic guide 134 for a given weight range along with prescription and dosage information.

Figure 12:
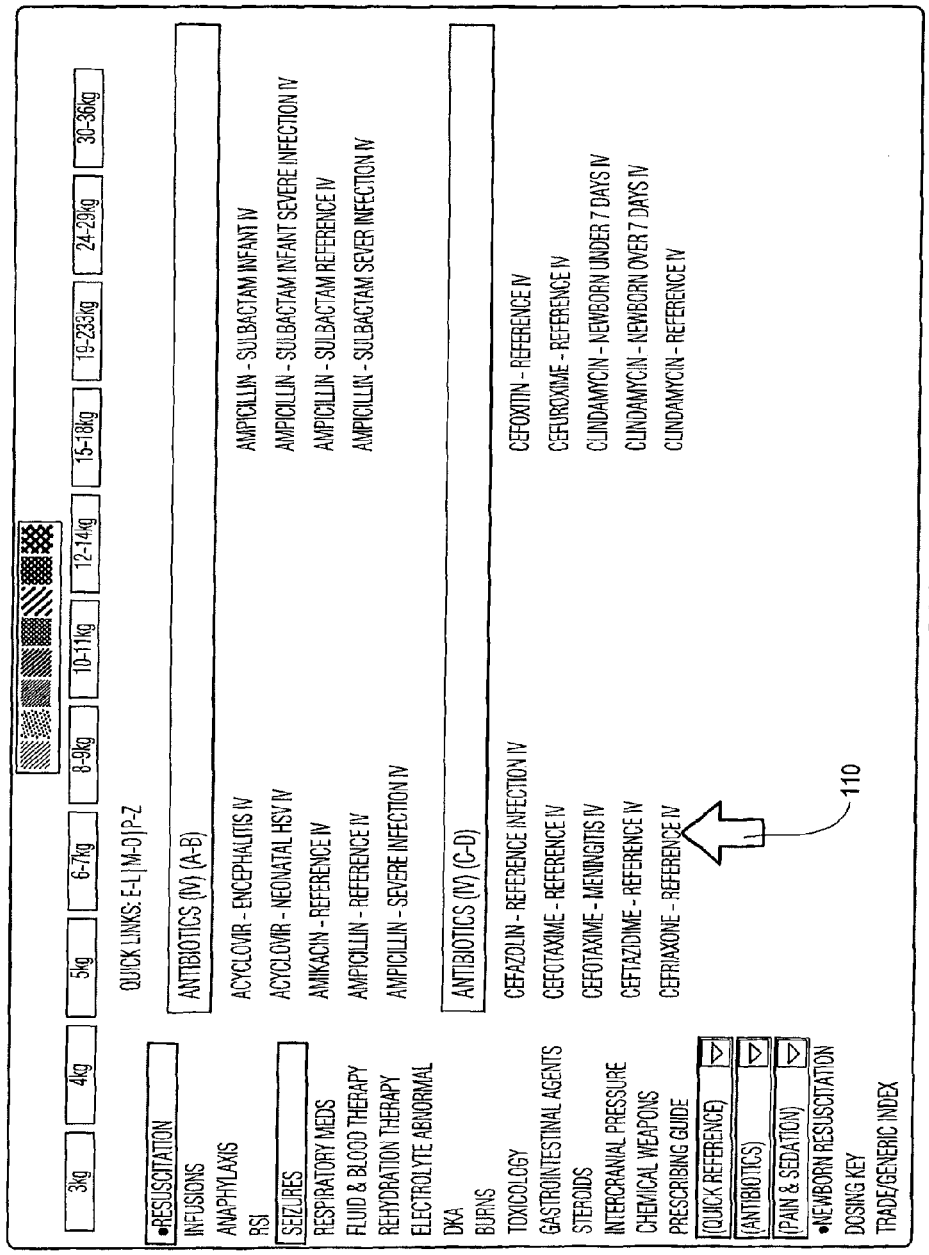
FIG. 12 is a representation of a listing of common antibiotics according to an embodiment of the invention.

FIG. 12 discloses a listing of specific antibiotics for different weight ranges, child types, and conditions 132. Once the antibiotic is selected 110, the grid is displayed 112 for that particular weight range and drug, while hiding other inapplicable doses 114.

Figure 13:
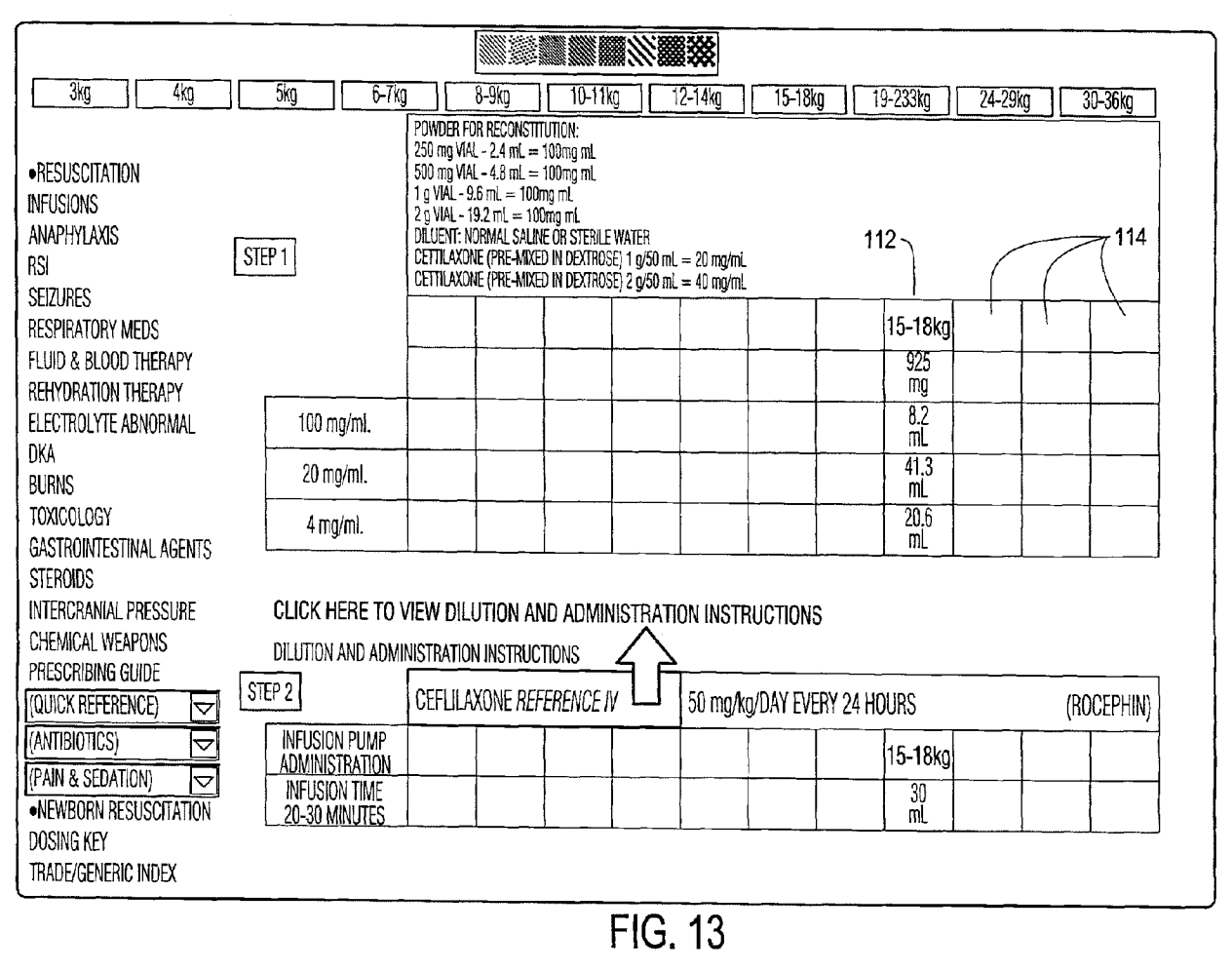

FIG. 13 represents a step whereby drug dilution and administration instructions are accessed and displayed.

Figure 14:
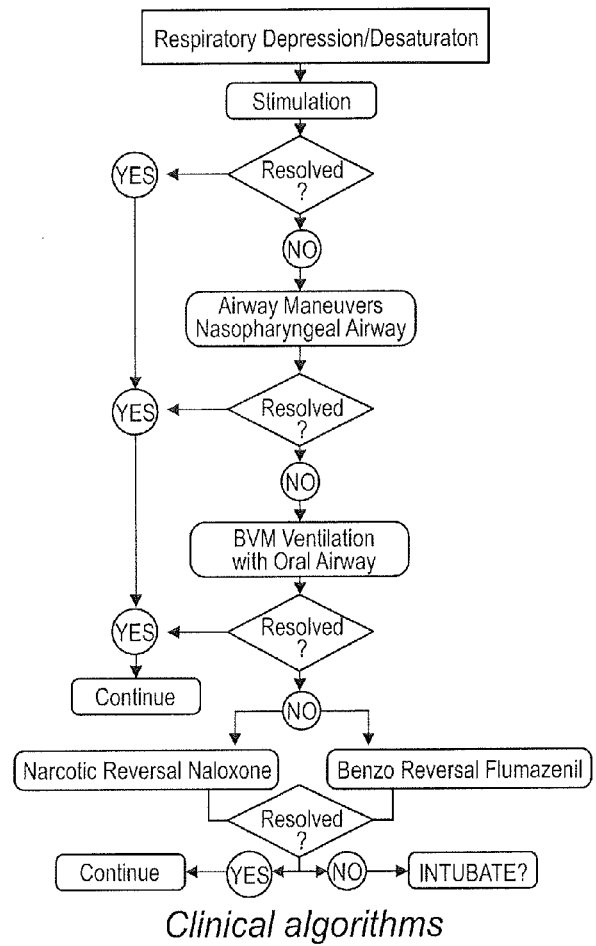
FIG. 14 is a representation of a diagnosis guide displaying a diagnosis flowchart according to an embodiment of the invention.

FIG. 14 shows a representation of a diagnosis and treatment guide displaying a treatment flowchart according to an embodiment, such as a clinical algorithm for diagnosis and/or treatment of, for example, respiratory depression/desaturation.

Figure 15:
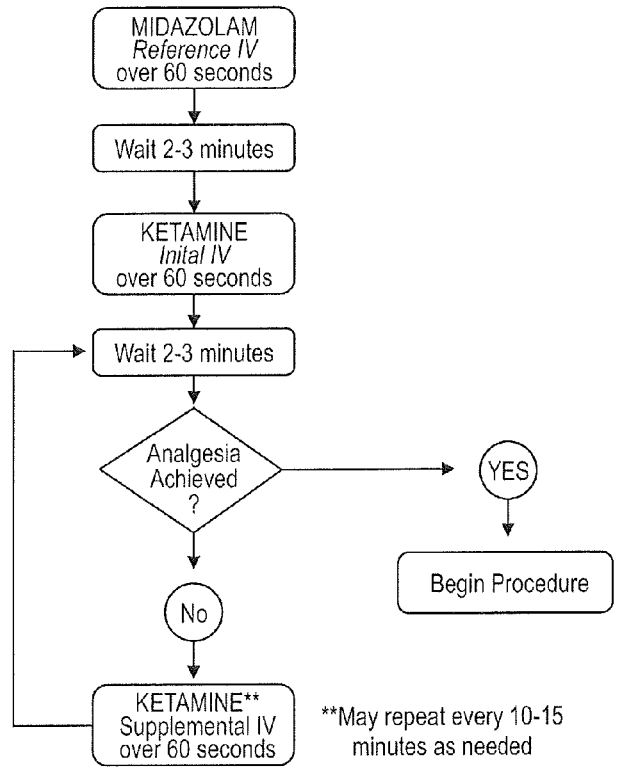
FIG. 15 is a representation of a treatment guide displaying a treatment flowchart according to an embodiment of the invention.

FIG. 15 shows a representation of a diagnosis and treatment guide displaying a treatment flowchart according to an embodiment, such as a flowchart 118 for the administration of midazolam followed by ketamine.

Figure 16:
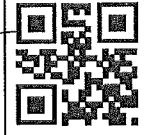
FIG. 16 is a representation of an entry screen according to an embodiment of the invention that initiates operation of the system to determine an infusion pump setting.

Referring now to FIGS. 16 and 17, the entry screen illustrated above is used to click on "Infusions", just below the "Resuscitation" selection tab. Beginning with entry screen 160, the matrix barcode 162 is scanned using, for example, a smart phone "P" containing or electronically connected to a database containing information necessary to provide necessary dosing information regarding drugs to be infused using an infusion pump.

As illustrated in FIG. 17, scanning the matrix code returns an app screen from which the user can select a weight range of the patient, for example, 8-9 kg. Also as shown, the appropriate weight range can be selected using the widely-used Broselow tape colors, and selecting on the proper Broselow color. The weight ranges can also be selected from the entry screen by color or weight range tabs, as shown on FIG. 18. A slider 168 having a range between 1 and 10 indicates that the dosage is in the high but correct range of dosages for the particular patient based on that patient's individual characteristics as input into the computer.

Figure 18:
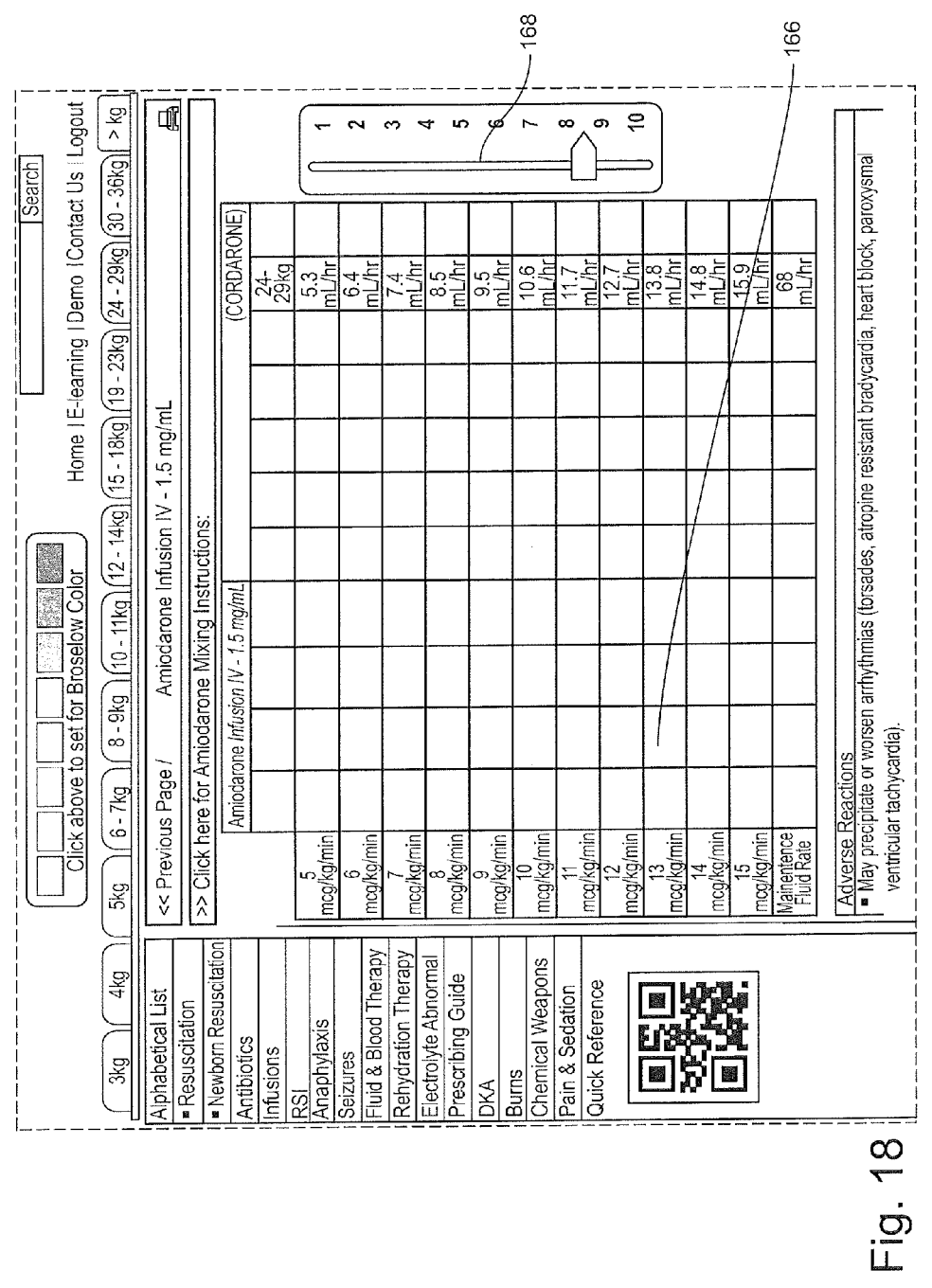

As also shown on FIG. 18, a patient in the weight range of 24-29 kg is selected. The physician indicates the intention to prescribe Amiodarone Infusion IV −1.5 mg/mL concentration. The proper dosage for a patient weighing between 24-29 kg is shown as being 13 mcg/kg/min, or 13.8 mL/hr. Thus, the conversion takes place immediately within the computer and without the need for the user to do a mathematical conversion.

Referring to FIG. 19, the smart phone "P" application displays a thumbnail view of Amiodarone Infusion IV −3 mg/mL concentration for a 5 kg pediatric patient, together with a listing of adverse reactions and contraindications and warnings at the bottom of the page.

Figure 20:
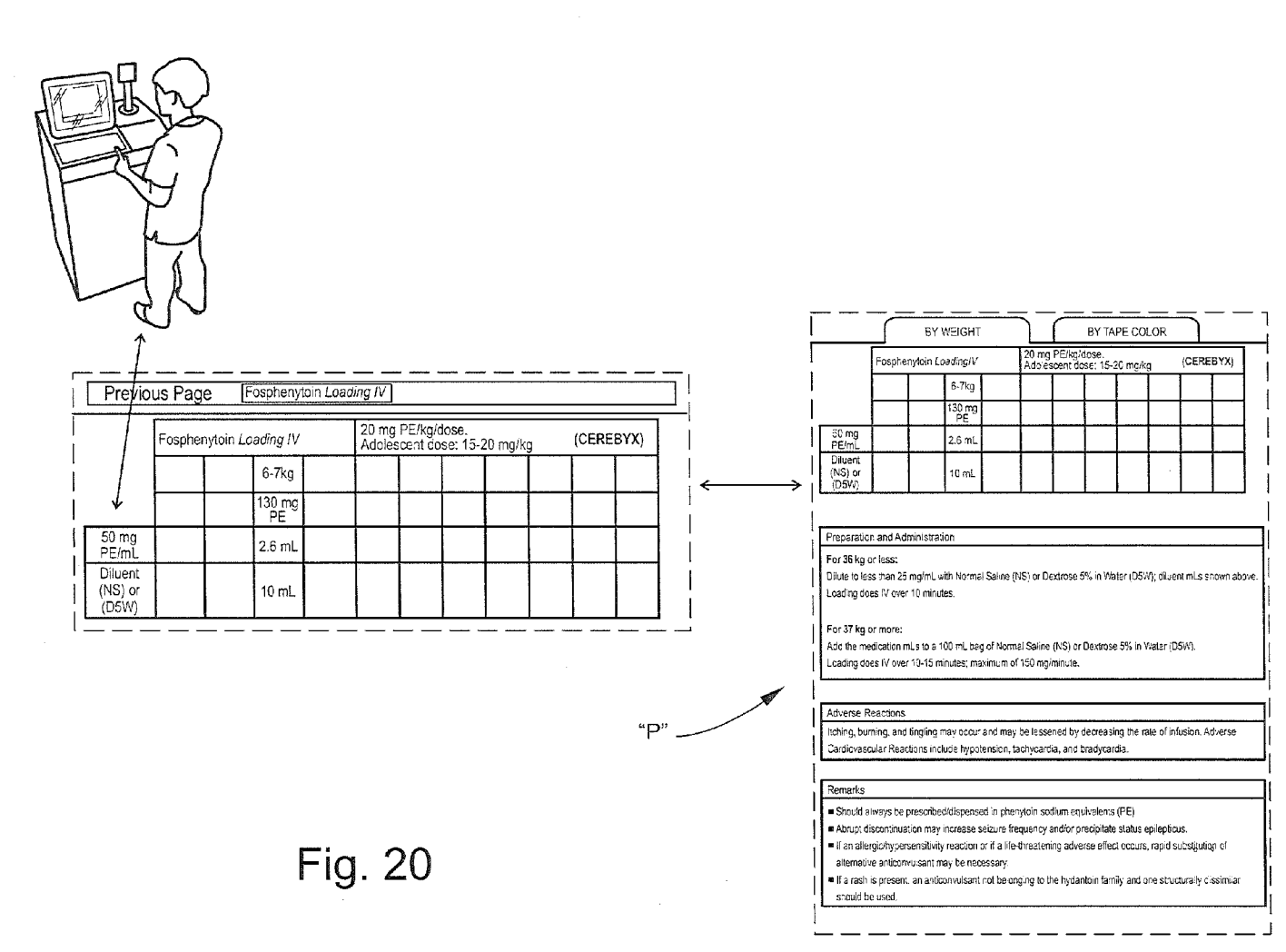

Another example is shown in FIG. 20, where a 6-7 kg pediatric patient is to be administered Fosphenytoin Loading IV. The user goes to the entry screen 160 and scans the NDC barcode to confirm the dose in mLs for the available concentrations. The smart phone application provides the required confirmation, and also information regarding the preparation and administration of the drug, its adverse reactions and remarks.

As shown in FIG. 21, a barcode printer prints a matrix barcode label with an adhesive backing that is applied directly to the infusion bag. This label contains the patient name and weight as well as full information regarding the drug, concentration and dosage.

Figure 22:
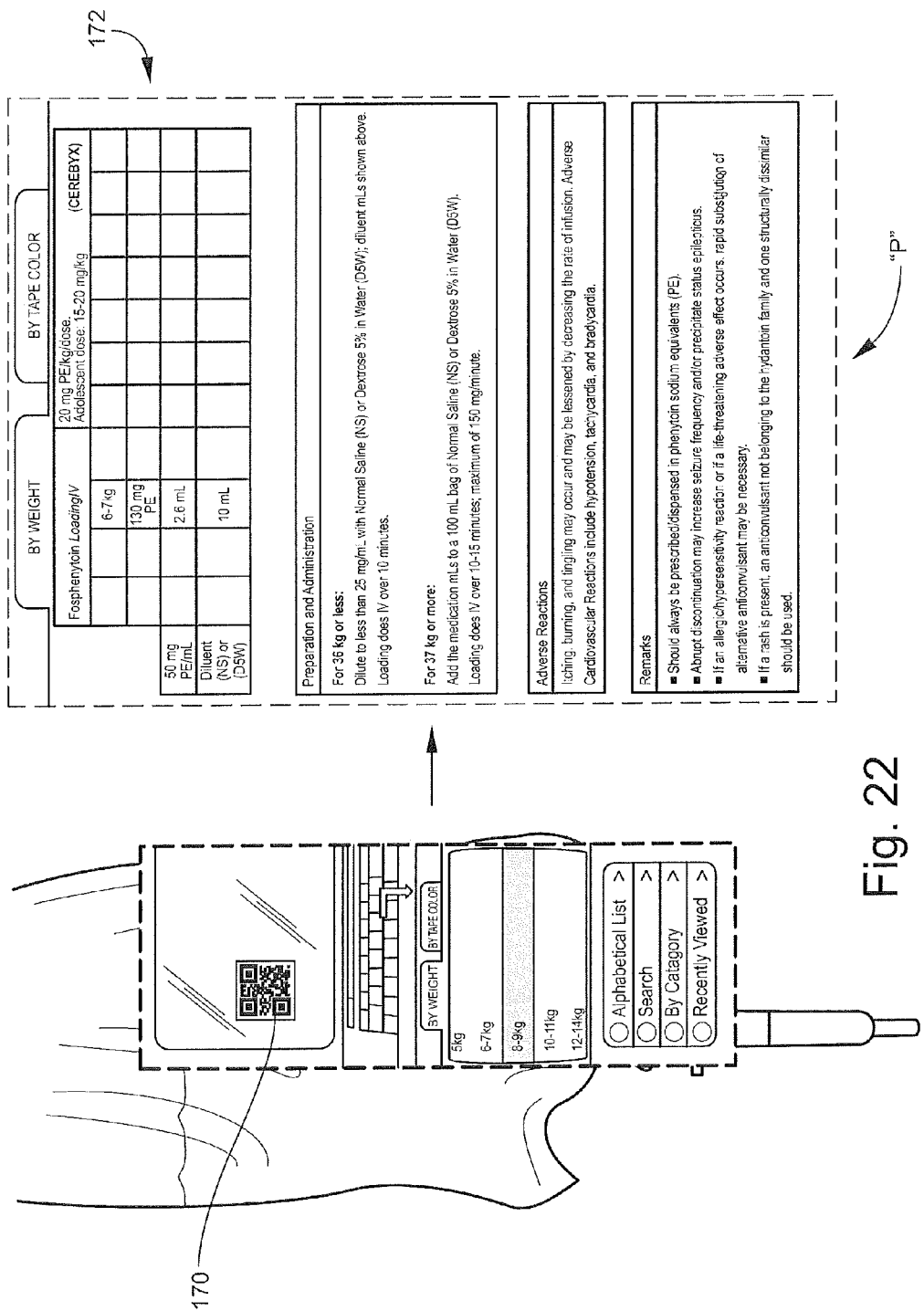
FIG. 22 illustrates transfer of drug and drug dosage information from the matrix barcode label on the infusion bag to an application screen.
Figure 23:
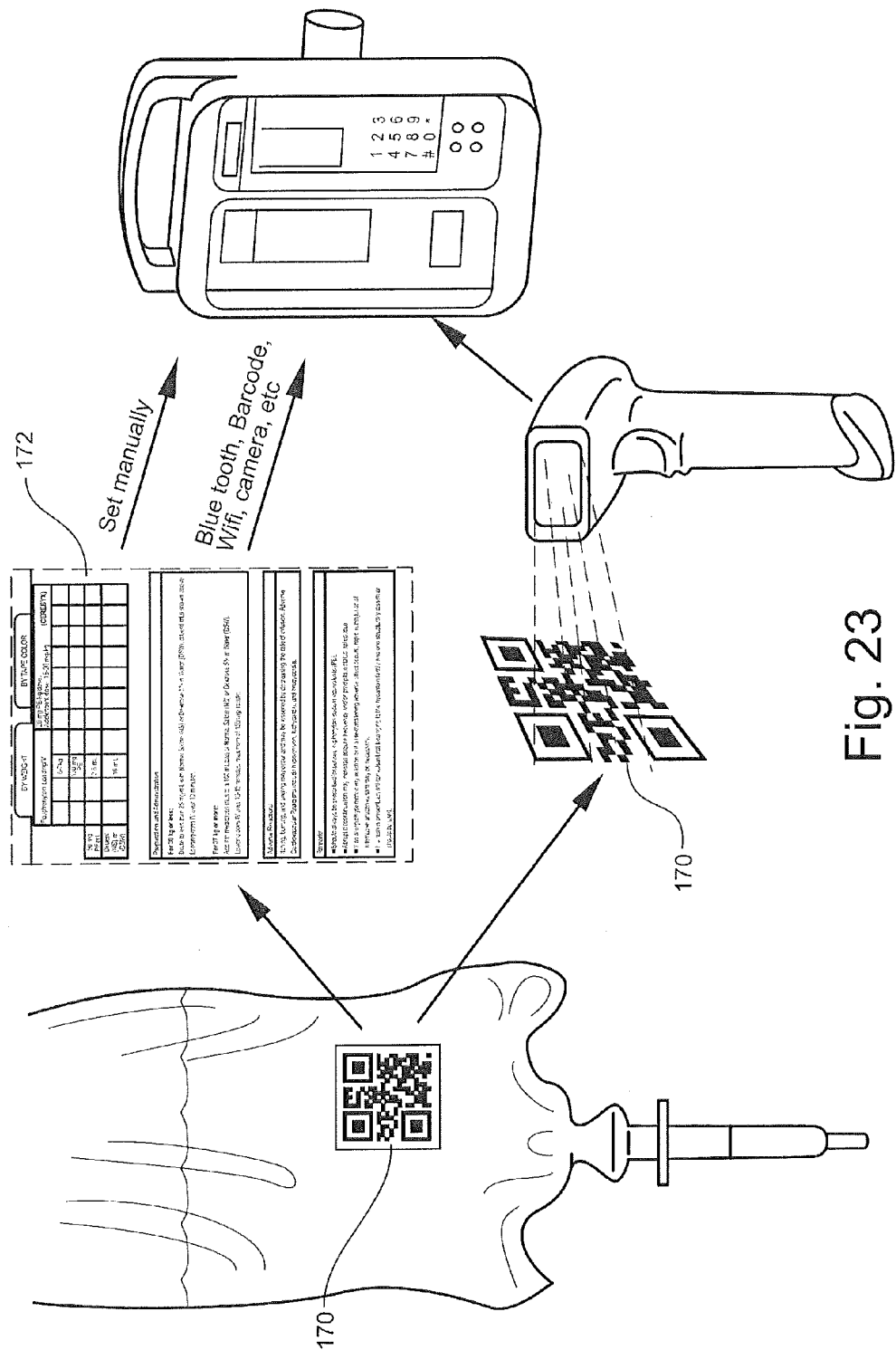
FIG. 23 illustrates transfer of drug and drug dosage information from the matrix barcode label on the infusion bag to an application screen, and then either manually or electronically to the infusion pump.

In FIG. 22 the process is reversed. By scanning the label 170 the information on the label 170 is transferred to the application in the smart phone "P" for use, in the form of an information page 172. FIG. 23 illustrates transfer of drug and drug dosage information from the matrix barcode label on the infusion bag to an application screen, and then either manually or electronically to the infusion pump.

Then, the nurse uses the information on the page 172 to manually set the infusion pump to the correct administration values. Alternatively, the label 170 can be scanned by a scanning device that outputs a signal, such as Bluetooth, WiFi, etc. that is transmitted to an infusion pump of the type equipped to automatically set the appropriate values in the infusion pump.

Figure 24:
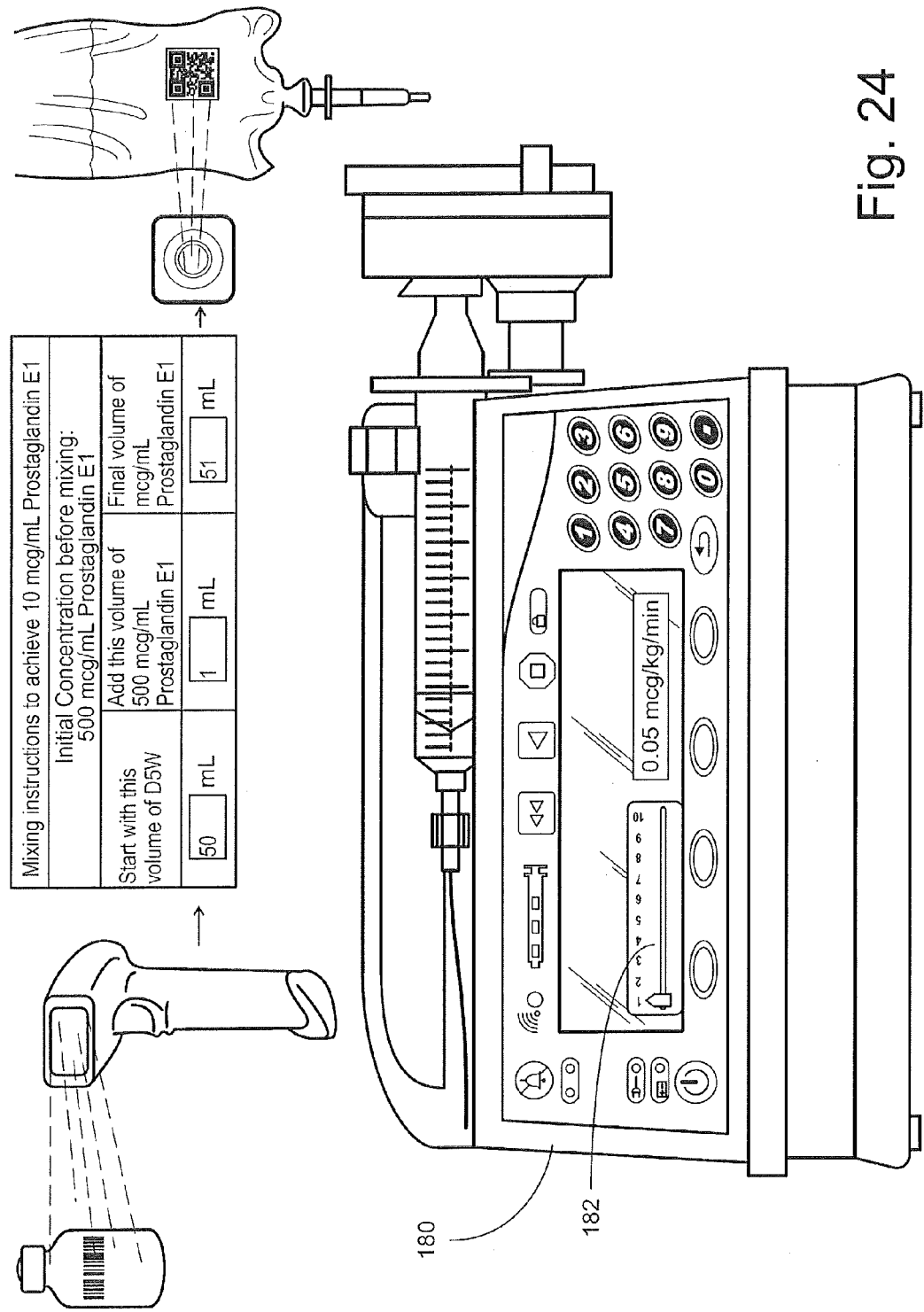
FIG. 24 illustrates one manner in which drug dosage information may be displayed on the infusion pump, including a "1-10" scale.

As shown in FIG. 24, an infusion pump 180 is provided with a "1-10" slider 182, such as the slider 168 shown in FIG. 18, from which is can be instantly visually determined that the dosage is in the correct range of dosages for the particular patient based on that patient's individual characteristics as input into the computer. As shown, a drug container is scanned and the computer returns proper mixing instructions, for example, to achieve 10 mcg/mL Prostaglandin E1. A readable label containing the appropriate information is applied to the infusion bag, which can then be read and the information digitally transferred to the infusion pump 180.

The slider 182 provides a visual indication that the dosage is in the proper range, as described above.

From the foregoing it is shown that determination of medical treatment values without data entry may be accomplished. The computerized system permits the identification of all of the independent variables that are needed to prescribe order, prepare and administer a medication for each drug, clinical variable, indication, route of administration, and potency while addressing therapeutic and/or regulatory and compliance requirements. The computerized system also permits input variables that are needed to prescribe order, prepare and administer a medication for each drug, clinical variable, indication, route of administration, and potency and permits use of this information manually or by barcode scanning to identify the appropriate clinical activity.

Preferably, the output for each appropriate clinical activity is provided with a unique identifier represented as a barcode. The computerized system uses the unique barcode, for example, to communicate the entire process to a digital system to translate back into a clinically relevant readable format and/or to automatically set a medication delivery device, such as an infusion pump.

The computerized system also optionally uses a relative potency scale to prescribe, order, or modify, or communicate medications orders or delivery irrespective of the relative strengths of each individual medication unit.

A computerized method of determining and entering treatment values in infusion pumps is disclosed above. Various details of the invention may be changed without departing from the scope of the invention. Furthermore, the foregoing description of the preferred embodiment of the invention and best mode for practicing the invention are provided for the purpose of illustration only and not for the purpose of limitation, the invention being defined by the claims.

I claim:

1. A computerized method of providing patient treatment values in real time, comprising the steps of:
   (a) providing a computer having a database containing digital information comprising a plurality of predetermined, non-individual patient selection criteria, clinical indication, drug selection, dosing values and administration information;
   (b) instructing the computer to select from the database provided in step (a) a desired non-individual patient criterion and drug representing a desired drug treatment for a specific patient;
   (c) determining in real time from the selected patient selection criterion and drug selection a medically-appropriate drug dosing value and drug administration instructions for the specific patient;
   (d) generating in real time a unique code representing the drug dosing value and drug administration instructions; and
   (e) utilizing the unique code to provide information necessary to treat the patient with the drug according to the drug dosing value and administration instructions generated by the computer from digital information contained in the database.

2. A computerized method of providing patient treatment values according to claim 1, wherein the unique code comprises a barcode, and the barcode is utilized by scanning the barcode to display the drug dosing value and administration instructions on a visual display.

3. A computerized method of providing patient treatment values according to claim 1, wherein the plurality of predetermined patient selection criteria comprises body weight.

4. A computerized method of providing patient treatment values according to claim 1, wherein the plurality of predetermined patient selection criteria comprises a color indicative of a predetermined body weight range.

5. A computerized method of providing patient treatment values according to claim 1, wherein the unique code comprises a barcode and further wherein the method includes the step of scanning the barcode with a barcode reader that outputs a signal to an input device indicative of the drug dosing value and administration instructions.

6. A computerized method of providing patient treatment values according to claim 1, and including the step of displaying the information necessary to treat the patient with the drug according to the drug dosing value and administration instructions a display screen of an electronic handheld device.

7. A computerized method of providing patient treatment values according to claim 1, and including the step of utilizing the unique code to set the appropriate drug dosage for administration to the patient into an infusion pump.

8. A computerized method of providing patient treatment values according to claim 1, and including the step of providing an electronic slider scale visible on a computer display and having a predetermined range indicating that the dosage is in the correct range of dosages for a specific patient based on a desired drug treatment for a specific patient.

9. A computerized method of providing patient treatment values according to claim 1, and including the steps of printing a label having an image of the unique code thereon, and applying the label to an infusion bag associated with the patient.

10. A computerized method of providing patient treatment values according to claim 1, wherein the step of providing a computer having a database containing digital information, comprises the steps of:
    (a) providing a computer database containing a universe of possible drug dosages, frequencies and indications for a plurality of drugs;
    (b) determining for the plurality of drugs all of the medically appropriate combinations of drug dosages, frequencies and indications;
    (c) assigning a unique scannable code to each one of all of the medically appropriate combinations of drug dosages, frequencies and indications; and
    (d) scanning the unique code to communicate visible instructions the appropriate drug dosage, frequency and indication for administration to the specific patient to a care giver.

11. A computerized method of providing patient treatment values according to claim 1, and including the steps of:
    (a) determining in real time a patient condition category for a specific patient from the computer database;
    (b) used the selected patient condition category together with the selected patient criterion and selected drug to determine in real time a medically-appropriate drug dosing value and drug administration instructions for the specific patient;
    (c) generating in real time a unique code representing the drug dosing value and drug administration instructions for the selected patient condition category; and
    (d) utilizing the unique code to provide information necessary to treat the patient with the drug according to the drug dosing value and administration instructions generated by the computer from digital information contained in the database.

12. A computerized method of providing patient treatment values according to claim 11, wherein the plurality of predetermined patient selection criteria comprises body weight.

13. A computerized method of providing patient treatment values according to claim 11, wherein the plurality of predetermined patient selection criteria comprises a color indicative of a predetermined body weight range.

14. A computerized method of providing patient treatment values according to claim 11, wherein the unique code comprises a barcode and further wherein the method includes the step of scanning the barcode with a barcode reader that outputs a signal to an input device indicative of the drug dosing value and administration instructions.

15. A computerized method of providing patient treatment values according to claim 11, and including the step of displaying the information necessary to treat the patient with the drug according to the drug dosing value and administration instructions a display screen of an electronic handheld device.

16. A computerized method of providing patient treatment values according to claim 11, and including the step of utilizing the unique code to set the appropriate drug dosage for administration to the patient into an infusion pump.

17. A computerized method of providing patient treatment values according to claim 11, and including the step of providing an electronic slider scale visible on a computer display and having a predetermined range indicating that the dosage is in the correct range of dosages for a specific patient based on a desired drug treatment for a specific patient.

18. A computerized method of providing patient treatment values according to claim 11, and including the steps of printing a label having an image of the unique code thereon, and applying the label to an infusion bag associated with the patient.

19. A computerized method of providing patient treatment values according to claim 11, wherein the step of providing a computer having a database containing digital information, comprises the steps of:

(a) providing a computer database containing a universe of possible drug dosages, frequencies and indications for a plurality of drugs;

(b) determining for the plurality of drugs all of the medically appropriate combinations of drug dosages, frequencies and indications;

(c) assigning a unique scannable code to each one of all of the medically appropriate combinations of drug dosages, frequencies and indications; and (d) scanning the unique code to communicate visible instructions the appropriate drug dosage, frequency and indication for administration to the specific patient to a care giver.

* * * * *